United States Patent
Malcuit et al.

(10) Patent No.: US 10,457,950 B2
(45) Date of Patent: Oct. 29, 2019

(54) GENE TARGETING IN PLANTS USING A CHIMERIC MULTI DOMAIN RECOMBINATION PROTEIN

(75) Inventors: Isabelle Malcuit, London (GB); Alexander Sorokin, London (GB)

(73) Assignee: Algentech SAS, Envry (FR)

( * ) Notice: Subject to any disclaimer, the term of this patent is extended or adjusted under 35 U.S.C. 154(b) by 1303 days.

(21) Appl. No.: 13/146,159

(22) PCT Filed: Jan. 25, 2010

(86) PCT No.: PCT/GB2010/000111
§ 371 (c)(1),
(2), (4) Date: Oct. 7, 2011

(87) PCT Pub. No.: WO2010/084331
PCT Pub. Date: Jul. 29, 2010

(65) Prior Publication Data
US 2012/0042411 A1    Feb. 16, 2012

(30) Foreign Application Priority Data
Jan. 26, 2009    (GB) .................................. 0901249.3

(51) Int. Cl.
*C12N 15/82*    (2006.01)
(52) U.S. Cl.
CPC .............................. *C12N 15/8213* (2013.01)
(58) Field of Classification Search
None
See application file for complete search history.

(56) References Cited

U.S. PATENT DOCUMENTS

2005/0048652 A1    3/2005    Voytas et al.
2007/0031380 A1    2/2007    Hackett et al.

FOREIGN PATENT DOCUMENTS

| WO | WO 99/25840 A1 | 5/1999 | |
|----|----|----|----|
| WO | WO 00/70019 A2 | 11/2000 | |
| WO | WO-02/077246 A2 * | 10/2002 | ............. C12N 15/82 |
| WO | WO 02/077246 A2 | 10/2002 | |
| WO | WO 03/031629 A1 | 4/2003 | |
| WO | WO 03/093428 A2 | 11/2003 | |
| WO | WO 2004/009792 A2 | 1/2004 | |
| WO | WO-2008/006028 A2 * | 1/2008 | ................ C12N 9/88 |
| WO | WO-2009/006297 * | 1/2009 | ............. C12N 15/82 |
| WO | WO 2009/006297 A2 | 1/2009 | |

OTHER PUBLICATIONS

Albert et al 1995 (The Plant Journal 7:4 p. 649-659).*
Guo et al 1997 (Nature 389: p. 40-46).*
Tinland et al 1994 (PNAS 91: p. 8000-8004).*
Morrical 2015 (Cold Spring Harbor Perspectives in Biology 7: p. 1-20).*
J. W. Donovon, et al., Homotypic and Heterotypic Protein Associations Control Rad51 Function in Double-Strand Break Repair, Published by Cold Spring Harbor Laboratory Genes Dev. 1994 8:2552-2562.
Bermd Reiss, et al., Reca Protein Stimulates Homologous Recombination in Plants, Proc. Natl. Acad. Sci. USA, vol. 93, pp. 3094-3098, Apr. 1996, XP002023622.
Bernd Reiss, Homologous Recombination and Gene Targeting in Plant Cells, International Review of Cytology, Academic Press, vol. 228, pp. 85-139, Jan. 1, 2003, XP009125899.
International Search Report and Written Opinion corresponding to International Patent Application No. PCT/GB2010/000111, dated Jan. 26, 2009.
Kumar, et al, Gene Targeting in Plants: Fingers on the Move, Trends in plant Science, Elsevier Science, Oxford, vol. 11, No. 4, pp. 159-161, Apr. 1, 2006, XP005400839.
Michael Schlappi, et al., A Highly Sensitive Plant Hybrid Protein Assay System Based on the Spm Promotoer and TnpA Protein for Detection and Analysis of Transcription Activiation Domains, Plant Molecular Biology, vol. 32, pp. 717-725 1996.
Patrick Masson, et al., The tnpA and tnpD Gene Products of the Spm Element are Required for Transposition in Tobacco, The Plant Cell, vol. 3, pp. 73-85, Jan. 1991.
Shigeru Iida, et al., Modification of Endogenous Natural Genes by Gene Targeting in Rice and Other Higher Plants, Plant Molecular biology (2005), vol. 59, pp. 205-219.
Tovkach Andriy, et al., A Toolbox and Procedural Notes for Characterizing Novel Zinc Finger Nucleases for Genome Editing in Plant Cells, Plant Journal, vol. 57, No. 4, pp. 747-757, Nov. 24, 2008, XP002591473.
Xiao Y-L, et al., Intrachromosomal Homologous Recombination in *Arabidopsis* Induced by a Maize Transposon, Molecular and General Genetics, vol. 263, No. 1, pp. 22-29, Feb. 1, 2000, XP002591474.

* cited by examiner

*Primary Examiner* — Matthew R Keogh
(74) *Attorney, Agent, or Firm* — Sughrue Mion, PLLC

(57) ABSTRACT

An isolated polynucleotide sequence that encodes for a multi domain recombination protein, comprising a donor DNA-Binding domain (BDB); and a chromosomal binding domain (CBD). A plant cell can be transformed by introducing into the cell a first nucleic acid sequence, which comprises a plant nuclear promoter operably linked to a first nucleic acid sequence comprising the stated polynucleotide sequence, and a second nucleic acid sequence, which comprises a donor nucleic acid sequence and at least two flanking sequences capable of binding to a donor binding domain of the protein, the sequences being located adjacent to each end of the donor polynucleotide sequence forming left and right borders thereto.

Figure 1:
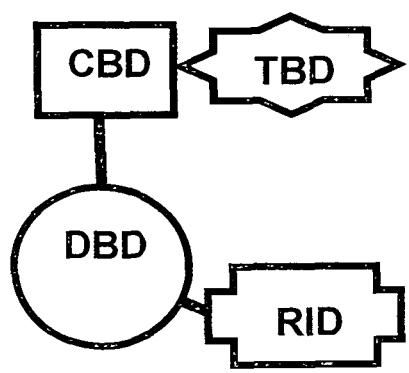

20 Claims, 8 Drawing Sheets
Specification includes a Sequence Listing.

(A)

(B)

SEQUENCE LISTING

<160> NUMBER OF SEQ ID NOS: 84

<210> SEQ ID NO 1
<211> LENGTH: 31
<212> TYPE: DNA
<213> ORGANISM: Artificial sequence
<220> FEATURE:
<223> OTHER INFORMATION: Synthetic oligonucleotide primer AS900

<400> SEQUENCE: 1
gctcgagaac atgttcagga tggattcgtc t          31

<210> SEQ ID NO 2
<211> LENGTH: 32

<212> TYPE: DNA
<213> ORGANISM: Artificial sequence
<220> FEATURE:
<223> OTHER INFORMATION: Synthetic oligonucleotide primer AS101

<400> SEQUENCE: 2
cgcggatccg cgcatttgcc ctcctatcac ac                                    32

<210> SEQ ID NO 3
<211> LENGTH: 1638
<212> TYPE: DNA
<213> ORGANISM: Zea mays

<400> SEQUENCE: 3
atgttcagga tggattcgtc tggcaggaga tccagatcac gaaggtcgag gggttccagt      60
ggtgctccta acatgtttga gggcaccaca acaagcagaa gcaggcaaga gcagttgctt     120
gcctcccttg agcagatgcg gggtagcagc ggaccctcca atacagaagg gactacttcg     180
cgtgccgctg atttggtggc acctactatg cacctactg cggaggcagc tgtgacgcg       240
gaggcagctg tggacgcgga ggctgaggaa gctgccgcag aactggacga tggagaggag     300
acttcgggag cagacgcttc tacagaggag gctgccacac aggctccgcc acggcgtgcc     360
atcagatatc gtcggtccct cacattgaag ccttctaaac ccttcgatca acggagggtt     420
attgaaccga aaggcaccag ggcgtggaag gaggtcagtt gggacggaac agggcatcgc     480
acaccaatcc tcacagagtt ggggatttgt ttgcgattcg cctacccggc gatggtgaca     540
gagggcggtc aagagatagc tgctcattac tgggctcatt gggatctcaa gccgtacggg     600
aacgacggga cacacacaag caaagtgtgg gatttgtttt ggggccaatt tcgcgtgtgc     660
gaccctata ccttggatga ttcatatgtg cgtgaggtat tcaatggctc agcagataga      720
gctgtaaagg gaatgatgta taagcacga ttgagggccg tcacggtgta ccaaaagcgt      780
cagggaact attgtgacgc gaatatggca aaggaaattc acctgacggc tcagcagtac      840
aaagagagtg aggtggattg gttgagccac cattcggatg cttgggcgtg gatgtgcgag     900
tatgggctt ctgaggagtt cttggccata tctaataaga atcgtatgaa tcggttgagc      960
aagccagggg tccacttctt cggggcggat ggacacgttg gcaaggctgc acgtatggcg    1020
gctcgaaatg gagtggagcc tactttgctt caagtcttcg tcgagggaca caagggtccc    1080
gatccgaatc atccggaaat actgaatgac agtaatgcga cagagaaact ggctcgctac    1140
attgacaacg tgagagaaaa aaatggtcca gacacggatt ggctcactgg agagttcgat    1200
acggaggcgc ttataaaggc tggtggaggc gtaccacatg ggaggttagc aattggtgac    1260
ggtgttgtcc cccgtcggag ttacactaga cggtccaatt tctcagctgg gtcgaatcga    1320
ccccgacgac catctgcacg tgaaggagag ctgcttgaga gatgactca gatggaggag     1380
agtatggcgc aatataagca acaagtgcag caacagatgc aacaaatgca aaattggatg    1440
ctacatcaga tgtatggagg tgccggaact cagttcggca tgccgccttt tcaacaaccc    1500
cctatcatca cacatccggt gtctggacaa tcatcggacc gctccactgc agcggcagat    1560
ggatcacagg gttctgcaac ttctgtccaa gaccaattga tgccattggg tgtgatcggc    1620
gggcaaatgc gcggatcc                                                  1638

<210> SEQ ID NO 4
<211> LENGTH: 147
<212> TYPE: DNA
<213> ORGANISM: Escherichia coli

```
<400> SEQUENCE: 4
ggtaacctga agcagtccaa cacgctgctg atcttcatca accagatccg tatgaaaatt      60
ggtgtgatgt tcggtaaccc ggaaaccact accggtggta acgcgctgaa attctacgcc     120
tctgttcgtc tcgacatccg tcgttac                                         147

<210> SEQ ID NO 5
<211> LENGTH: 30
<212> TYPE: DNA
<213> ORGANISM: Artificial sequence
<220> FEATURE:
<223> OTHER INFORMATION: Synthetic oligonucleotide primer AS380

<400> SEQUENCE: 5
cgggatccgg taacctgaag cagtccaaca                                       30

<210> SEQ ID NO 6
<211> LENGTH: 32
<212> TYPE: DNA
<213> ORGANISM: Artificial sequence
<220> FEATURE:
<223> OTHER INFORMATION: Synthetic oligonucleotide primer AS381

<400> SEQUENCE: 6
cggtctagat ttaacgacgg atgtcgagac ga                                    32

<210> SEQ ID NO 7
<211> LENGTH: 49
<212> TYPE: DNA
<213> ORGANISM: Artificial sequence
<220> FEATURE:
<223> OTHER INFORMATION: Synthetic oligonucleotide primer AS881

<400> SEQUENCE: 7
ctctcgcgtt tgcgttcact cggttctcca tcatcatctt cacgcggac                  49

<210> SEQ ID NO 8
<211> LENGTH: 23
<212> TYPE: DNA
<213> ORGANISM: Artificial sequence
<220> FEATURE:
<223> OTHER INFORMATION: Synthetic oligonucleotide primer AS882

<400> SEQUENCE: 8
cactagttca tctctcgcgt ttg                                              23

<210> SEQ ID NO 9
<211> LENGTH: 48
<212> TYPE: DNA
<213> ORGANISM: Artificial sequence
<220> FEATURE:
<223> OTHER INFORMATION: Synthetic oligonucleotide primer AS899

<400> SEQUENCE: 9
ccatcatcat cttcacgcgg acgcttgtaa cgacggatgt cgagacga                   48

<210> SEQ ID NO 10
<211> LENGTH: 57
<212> TYPE: DNA
<213> ORGANISM: Agrobacterium tumefaciens

<400> SEQUENCE: 10
aagcgtccgc gtgaagatga tgatggagaa ccgagtgaac gcaaacgcga gagatga         57
```

<210> SEQ ID NO 11
<211> LENGTH: 1842
<212> TYPE: DNA
<213> ORGANISM: Artificial sequence
<220> FEATURE:
<223> OTHER INFORMATION: Synthetic polynucleotide encoding tnpA-recA-
      virD2NLS domain fusion

<400> SEQUENCE: 11

```
atgttcagga tggattcgtc tggcaggaga tccagatcac gaaggtcgag gggttccagt      60
ggtgctccta acatgtttga gggcaccaca acaagcagaa gcaggcaaga gcagttgctt    120
gcctcccttg agcagatgcg gggtagcagc ggaccctcca atacagaagg gactacttcg    180
cgtgccgctg atttggtggc acctactatg gcacctactg cggaggcagc tgtggacgcg    240
gaggcagctg tggacgcgga ggctgaggaa gctgccgcag aactggacga tggagaggag    300
acttcgggag cagacgcttc tacagaggag gctgccacac aggctccgcc acggcgtgcc    360
atcagatatc gtcggtccct cacattgaag ccttctaaac ccttcgatca acggagggtt    420
attgaaccga aaggcaccag ggcgtggaag gaggtcagtt gggacggaac agggcatcgc    480
acaccaatcc tcacagagtt ggggatttgt ttgcgattcg cctacccggc gatggtgaca    540
gagggcggtc aagagatagc tgctcattac tgggctcatt gggatctcaa gccgtacggg    600
aacgacggga cacacacaag caaagtgtgg gatttgtttt ggggccaatt cgcgtgtgc     660
gaccccctata ccttggatga ttcatatgtg cgtgaggtat tcaatggctc agcagataga    720
gctgtaaagg gaatgatgta taaagcacga ttgagggccg tcacggtgta ccaaaagcgt    780
cagggggaact attgtgacgc gaatatggca aaggaaattc acctgacggc tcagcagtac    840
aaagagagtg aggtggattg gttgagccac cattcggatg cttgggcgtg gatgtgcgag    900
tatttgggctt ctgaggagtt cttggccata tctaatagaa atcgtatgaa tcggttgagc    960
aagccagggg tccacttctt cggggcggat ggacacgttg gcaaggctgc acgtatggcg   1020
gctcgaaatg gagtggagcc tactttgctt caagtcttcg tcgagggaca caagggtccc   1080
gatccgaatc atccggaaat actgaatgac agtaatgcga cagagaaact ggctcgctac   1140
attgacaacg tgagagaaaa aaatggtcca gacacggatt ggctcactgg agagttcgat   1200
acggaggcgg cttataaggc tggtggaggc gtaccacatg ggaggttagc aattggtgac   1260
ggtgttgtcc cccgtcggag ttacactaga cggtccaatt tctcagctgg gtcgaatcga   1320
ccccgacgac catctgcacg tgaaggagag ctgcttgaga gatgactca gatggaggag   1380
agtatggcgc aatataagca acaagtgcag caacagatgc aacaaatgca aaattggatg   1440
ctacatcaga tgtatggagg tgccggaact cagttcggca tgccgccttt tcaacaaccc   1500
cctatcatca cacatccggt gtctggacaa tcatcggacc gctccactgc agcggcagat   1560
ggatcacagg gttctgcaac ttctgtccaa gaccaattga tgccattggg tgtgatcggc   1620
gggcaaatgc gcggatccgg taacctgaag cagtccaaca cgctgctgat cttcatcaac   1680
cagatccgta tgaaaattgg tgtgatgttc ggtaacccgg aaaccactac cggtggtaac   1740
gcgctgaaat tctacgcctc tgttcgtctc gacatccgtc gttacaagcg tccgcgtgaa   1800
gatgatgatg gagaaccgag tgaacgcaaa cgcgagagat ga                      1842
```

<210> SEQ ID NO 12
<211> LENGTH: 28
<212> TYPE: DNA
<213> ORGANISM: Artificial sequence
<220> FEATURE:
<223> OTHER INFORMATION: Synthetic oligonucleotide primer AS724

```
<400> SEQUENCE: 12
cggtacctac cggatttgga gccaagtc                                           28

<210> SEQ ID NO 13
<211> LENGTH: 42
<212> TYPE: DNA
<213> ORGANISM: Artificial sequence
<220> FEATURE:
<223> OTHER INFORMATION: Synthetic oligonucleotide primer AS726

<400> SEQUENCE: 13
gctcgagtgt tggtgacct gaaataaaac aatagaacaa gt                            42

<210> SEQ ID NO 14
<211> LENGTH: 1738
<212> TYPE: DNA
<213> ORGANISM: Arabidopsis thaliana

<400> SEQUENCE: 14
taccggattt ggagccaagt ctcataaacg ccattgtgga agaaagtctt gagttggtgg        60
taatgtaaca gagtagtaag aacagagaag agagagagtg tgagatacat gaattgtcgg       120
gcaacaaaaa tcctgaacat cttattttag caaagagaaa gagttccgag tctgtagcag       180
aagagtgagg agaaatttaa gctcttggac ttgtgaattg ttccgcctct tgaatacttc       240
ttcaatcctc atatattctt cttctatgtt acctgaaaac cggcatttaa tctcgcgggt       300
ttattccggt tcaacatttt ttttgttttg agttattatc tgggcttaat aacgcaggcc       360
tgaaataaat tcaaggccca actgttttt tttttaagaa gttgctgtta aaaaaaaaa        420 aagggaatta acaacaacaa caaaaaaga taaagaaaat aataacaatt actttaattg       480
tagactaaaa aaacatagat tttatcatga aaaaagaga aagaaataa aaacttggat        540 caaaaaaaa acatacagat cttctaatta ttaacttttc ttaaaaatta ggtccttttt       600
cccaacaatt aggtttagag ttttggaatt aaaccaaaaa gattgttcta aaaatactc        660 aaatttggta gataagtttc cttattttaa ttagtcaatg gtagatactt ttttttcttt      720
tctttattag agtagattag aatcttttat gccaagtatt gataaattaa atcaagaaga      780
taaactatca taatcaacat gaaattaaaa gaaaatctc atatatagta ttagtattct       840
ctatatatat tatgattgct tattcttaat gggttgggtt aaccaagaca tagtcttaat      900
ggaaagaatc tttttgaac ttttccttta tgattaaat tcttctatag aaagaaaga        960 aattattga ggaaagtat atacaaaaag aaaatagaa aatgtcagt gaagcagatg       1020 taatggatga cctaatccaa ccaccaccat aggatgtttc tacttgagtc ggtcttttaa     1080
aaacgcacgg tggaaaatat gacacgtatc atatgattcc ttcctttagt ttcgtgataa     1140
taatcctcaa ctgatatctt ccttttttg ttttggctaa agatatttta ttctcattaa     1200
tagaaaagac ggttttgggc ttttggtttg cgatataaag aagaccttcg tgtggaagat     1260
aataattcat cctttcgtct ttttctgact cttcaatctc tcccaaagcc taaagcgatc     1320
tctgcaaatc tctcgcgact ctctctttca aggtatattt tctgattctt tttgtttttg     1380
attcgtatct gatctccaat ttttgttatg tggattattg aatcttttgt ataaattgct     1440
tttgacaata ttgttcgttt cgtcaatcca gcttctaaat tttgtcctga ttactaagat     1500
atcgattcgt agtgtttaca tctgtgtaat ttcttgcttg attgtgaaat taggattttc     1560
aaggacgatc tattcaattt tgtgttttc tttgttcgat tctctctgtt ttaggtttct     1620
```

```
tatgtttaga tccgtttctc tttggtgttg ttttgatttc tcttacggct tttgatttgg    1680
tatatgttcg ctgattggtt tctacttgtt ctattgtttt atttcaggtc accaaaca     1738
```

<210> SEQ ID NO 15
<211> LENGTH: 406
<212> TYPE: DNA
<213> ORGANISM: Artificial sequence
<220> FEATURE:
<223> OTHER INFORMATION: Synthetic sequence: Agropine synthase polyA
      signal (ags terminator) based on the gene bank sequence EU181145

<400> SEQUENCE: 15

```
gaattaacag aggtggatgg acagacccgt tcttacaccg gactgggcgc gggataggat    60
attcagattg ggatgggatt gagcttaaag ccggcgctga gaccatgctc aaggtaggca    120
atgtcctcag cgtcgagccc ggcatctatg tcgagggcat tggtggagcg cgcttcgggg    180
ataccgtgct tgtaactgag accggatatg aggccctcac tccgcttgat cttggcaaag    240
atatttgacg catttattag tatgtgttaa ttttcatttg cagtgcagta ttttctattc    300
gatctttatg taattcgtta caattaataa atattcaaat cagattattg actgtcattt    360
gtatcaaatc gtgtttaatg gtatttttta ttataatatt gatgat                   406
```

<210> SEQ ID NO 16
<211> LENGTH: 27
<212> TYPE: DNA
<213> ORGANISM: Artificial sequence
<220> FEATURE:
<223> OTHER INFORMATION: Synthetic oligonucleotide primer AS710

<400> SEQUENCE: 16

```
aagcttggga agtatgaaga cgtgaag                                        27
```

<210> SEQ ID NO 17
<211> LENGTH: 43
<212> TYPE: DNA
<213> ORGANISM: Artificial sequence
<220> FEATURE:
<223> OTHER INFORMATION: Synthetic oligonucleotide primer AS711

<400> SEQUENCE: 17

```
tttttttcgg gccatccggt ttatgaaagt tgtactaata tat                      43
```

<210> SEQ ID NO 18
<211> LENGTH: 22
<212> TYPE: DNA
<213> ORGANISM: Artificial sequence
<220> FEATURE:
<223> OTHER INFORMATION: Synthetic oligonucleotide primer AS712

<400> SEQUENCE: 18

```
accggatggc ccgaaaaaaa tg                                             22
```

<210> SEQ ID NO 19
<211> LENGTH: 27
<212> TYPE: DNA
<213> ORGANISM: Artificial sequence
<220> FEATURE:
<223> OTHER INFORMATION: Synthetic oligonucleotide primer AS713

<400> SEQUENCE: 19

```
ggtaccttat aattacatat acatgta                                        27
```

<210> SEQ ID NO 20

<211> LENGTH: 48
<212> TYPE: DNA
<213> ORGANISM: Artificial sequence
<220> FEATURE:
<223> OTHER INFORMATION: Synthetic oligonucleotide primer AS795

<400> SEQUENCE: 20
aggccaaaca aagatgaaaa ttacctggtt ggggatacca ggtcgaat         48

<210> SEQ ID NO 21
<211> LENGTH: 48
<212> TYPE: DNA
<213> ORGANISM: Artificial sequence
<220> FEATURE:
<223> OTHER INFORMATION: Synthetic oligonucleotide primer AS796

<400> SEQUENCE: 21
attcgacctg gtatccccaa ccaggtaatt ttcatctttg tttggcct         48

<210> SEQ ID NO 22
<211> LENGTH: 48
<212> TYPE: DNA
<213> ORGANISM: Artificial sequence
<220> FEATURE:
<223> OTHER INFORMATION: Synthetic oligonucleotide primer AS797

<400> SEQUENCE: 22
atgtttggat ggaaatgtgc tgacctgcaa tctcataagt acaatgga         48

<210> SEQ ID NO 23
<211> LENGTH: 48
<212> TYPE: DNA
<213> ORGANISM: Artificial sequence
<220> FEATURE:
<223> OTHER INFORMATION: Synthetic oligonucleotide primer AS798

<400> SEQUENCE: 23
tccattgtac ttatgagatt gcaggtcagc acatttccat ccaaacat         48

<210> SEQ ID NO 24
<211> LENGTH: 48
<212> TYPE: DNA
<213> ORGANISM: Artificial sequence
<220> FEATURE:
<223> OTHER INFORMATION: Synthetic oligonucleotide primer AS799

<400> SEQUENCE: 24
tcaagatggg aaaagatttc ttaccttcaa gaaacggggt ccagtcaa         48

<210> SEQ ID NO 25
<211> LENGTH: 48
<212> TYPE: DNA
<213> ORGANISM: Artificial sequence
<220> FEATURE:
<223> OTHER INFORMATION: Synthetic oligonucleotide primer AS800

<400> SEQUENCE: 25
ttgactggac cccgtttctt gaaggtaaga atcttttcc catcttga         48

<210> SEQ ID NO 26
<211> LENGTH: 48
<212> TYPE: DNA
<213> ORGANISM: Artificial sequence
<220> FEATURE:
<223> OTHER INFORMATION: Synthetic oligonucleotide primer AS801

<400> SEQUENCE: 26
tatctctagt ctctttttca agacctgcaa tgtttccacg catattat          48

<210> SEQ ID NO 27
<211> LENGTH: 48
<212> TYPE: DNA
<213> ORGANISM: Artificial sequence
<220> FEATURE:
<223> OTHER INFORMATION: Synthetic oligonucleotide primer AS802

<400> SEQUENCE: 27
ataatatgcg tggaaacatt gcaggtcttg aaaagagac tagagata          48

<210> SEQ ID NO 28
<211> LENGTH: 2352
<212> TYPE: DNA
<213> ORGANISM: Artificial sequence
<220> FEATURE:
<223> OTHER INFORMATION: Synthetic sequence: BCTVi sequence

<400> SEQUENCE: 28
ttataattac atatacatgt aaaaataacg tatataaaac gacataattc aaaacttgct    60
gagcaagttt cctgtggggc acacttactt tactttact aaagtaaagt tactttaata   120
aagttgtccc cttctttga ccagtcaaca atcttatct gaaaggaatc ttcttcagga    180
agtttcccgc aggaatcttc ttcaggaagt ttcccgctca aaaacgtcac atcattcaac   240
agtccccttc cacgtgtcac gttttgattg ggtgcccatt ttttcgggc catccggttt    300
atgaaagttg tactaatata tataatactc caatactcca atagatatgt taatatgcta   360
agccacgtca tcggagtaca atgcctccta ctaaaagatt tcgtattcaa gcaaaaaaca   420
tatttcttac atatcctcag tgttctcttt caaaagaaga agctcttgag caaattcaaa    480
gaatacaact ttcatctaat aaaaatata ttaaaattgc cagagagcta cacgaagatg   540
ggcaacctca tctccacgtc ctgcttcaac tcgaaggaaa agttcagatc acaaatatca    600
gattattcga cctggtatcc ccaaccaggt aattttcatc tttgtttggc cttccaagtg    660
cttttttttgc tgtttacggg tggaacttca gtaaaaatgg gatcaaaaca tcatatggca    720
taaataaatt ttaagaatgg cgaactcggg gttaccgaat atggcttcct ttttcagtgt    780
ttcttagtcc attgtactta tgagattgca ggtcagcaca tttccatcca aacattcaga    840
gagctaaatc cagctccgac gtcaagtcct acgtcgacaa ggacggagac acaattgaat    900
gggggagaatt ccagatcgac ggtagaagtg ctagaggagg tcaacagaca gctaacgact    960
catatgccaa ggcgttaaac gcaacttctc ttgaccaagc acttcaaata ttgaaggaag   1020
aacaaccaaa ggattacttc cttcaacatc acaatctttt gaacaatgct caaaagatat   1080
ttcagaggcc acctgatcca tggactccac tatttcctct gtcctcattc acaaacgttc   1140
ctgaggaaat gcaagaatgg gctgatgcat atttcggggt tgatgccgct gcgcggcctt   1200
taagatataa tagtatcata gtagagggtg attcaagaac agggaagact atgtgggcta   1260
gatctttagg ggcccacaat tacatcacag ggcacttaga ttttagccct agaacgtatt   1320
atgatgaagt ggaatacaac gtcattgatg acgtagatcc cacttactta aagatgaaac   1380
actggaaaca ccttattgga gcacaaaagg agtggcagac aaacttaaag tatgaaaaac   1440
cacgtgtcat taaggtggt atcccctgca ttatattatg caatccagga cctgagagct   1500
cataccaaca atttcttgaa aaaccagaaa atgaagccct taagtcctgg acattacata   1560
attcaacctt ctgcaaactc caaggtccgc tctttaataa ccaagcagca gcatcctcgc   1620

| | |
|---|---|
| aaggtgactc taccctgtaa ctgccacttc acaatacacc atgaatgtaa tagaggattt | 1680 |
| tcgcacaggg gaacctatta ctctccatca ggcaacaaat tccgtcgaat tcgagaatgt | 1740 |
| accgaatcca ctgtatatga aactcctatg gttcgagaga tacgggccaa tctatcaact | 1800 |
| gaagatacaa atcagattca actacaacct ccggagagcg ttgaatcttc acaagtgctg | 1860 |
| gatagagctg acgataactg gatcgaacag gatattgact ggaccccgtt tcttgaaggt | 1920 |
| aagaaatctt ttcccatctt gaagtcacct caaaccgaac gttaggaaat tccaaaatgt | 1980 |
| tttgatagta gtctacttag tttcaagttt tgggtttgtg tatactttca ctaataatat | 2040 |
| gcgtggaaac attgcaggtc ttgaaaaaga gactagagat atacttggat aatctaggtt | 2100 |
| taatttgtat taataatgta attagaggtt taaatcatgt cctgtatgaa gaatttactt | 2160 |
| ttgtatcaag tgtaattcag aaccagagtg ttgcaatgaa cttgtactaa tttcattatt | 2220 |
| aataataaat attattaata aaaatagcat ctacaattgc caaataatgt ggcatacata | 2280 |
| ttagtattat ccgtattatc attaacaaca acatagagta aagcattctc cttcacgtct | 2340 |
| tcatacttcc ca | 2352 |

<210> SEQ ID NO 29
<211> LENGTH: 1807
<212> TYPE: DNA
<213> ORGANISM: Artificial sequence
<220> FEATURE:
<223> OTHER INFORMATION: Synthetic sequence: uidA mutated gene

<400> SEQUENCE: 29

| | |
|---|---|
| atgttacgtc ctgtagaaac cccaacccgt gaaatcaaaa aactcgacgg cctgtgggca | 60 |
| ttcagtctgg atcgcgaaaa ctgtggaatt gatcagcgtt ggtgggaaag cgcgttacaa | 120 |
| gaaagccggg caattgctgt gccaggcagt tttaacgatc agttcgccga tgcagatatt | 180 |
| cgtaattatg cggcaacgt ctggtatcag cgcgaagtct ttataccgaa aggttgggca | 240 |
| ggccagcgta tcgtgctgcg tttcgatgcg gtcactcatt acggcaaagt gtgggtcaat | 300 |
| aatcaggaag tgatggagca tcagggcggc tatacgccat tgaagccga tgtcacgccg | 360 |
| tatgttattg ccgggaaaag tacgtatcac cgtttgtgtg aacaacgaac tgaactggca | 420 |
| gactatcccg ccgggaatgg tgattaccga cgaaaacggc aagaaaaagc agtcttactt | 480 |
| ccatgatttc tttaactatg ccggaatcca tcgcagcgta atgctctaca ccacgccgaa | 540 |
| cacctgggtg gacgatatca ccgtggtgac gcatgtcgcg caagactgta accacgcgtc | 600 |
| tgttgactgg caggtggtgg ccaatggtga tgtcagcgtt gaactgcgtg atgcggatca | 660 |
| acaggtggtt gcaactggac aaggcactag cgggactttg caagtggtga atccgcacct | 720 |
| ctggcaaccg ggtgaaggtt atctctatga actgtgcgtc acagccaaaa gccagacaga | 780 |
| gtgtgatatc tacccgcttc gcgtcggcat ccggtcagtg gcagtgaagg gcgaacagtt | 840 |
| cctgattaac cacaaaccgt tctactttac tggctttggt cgtcatgaag atgcggactt | 900 |
| acgtggcaaa ggattcgata cgtgctgat ggtgcacgac cacgcattaa tggactggat | 960 |
| tggggccaac tcctaccgta cctcgcatta cccttacgct gaagagatgc tcgactgggc | 1020 |
| agatgaacat ggcatcgtgg tgattgatga aactgctgct gtcggcttta acctctcttt | 1080 |
| aggcattggt ttcgaagcgg gcaacaagcc gaaagaactg tacagcgaag aggcagtcaa | 1140 |
| cgggaaaact cagcaagcgc acttacaggc gattaaagag ctgatagcgc gtgacaaaaa | 1200 |
| ccacccaagc gtggtgatgt ggagtattgc caacgaaccg gataccgtc gcaagtgca | 1260 |
| cgggaatatt tcgccactgg cggaagcaac gcgtaaactc gacccgacgc gtccgatcac | 1320 |

```
ctgcgtcaat gtaatgttct gcgacgctca caccgatacc atcagcgatc tctttgatgt    1380
gctgtgcctg aaccgttatt acggatggta tgtccaaagc ggcgatttgg aaacggcaga    1440
gaaggtactg gaaaaagaac ttctggcctg gcaggagaaa ctgcatcagc cgattatcat    1500
caccgaatac ggcgtggata cgttagccgg gctgcactca atgtacaccg acatgtggag    1560
tgaagagtat cagtgtgcat ggctggatat gtatcaccgc gtctttgatc gcgtcagcgc    1620
cgtcgtcggt gaacaggtat ggaatttcgc cgattttgcg acctcgcaag gcatattgcg    1680
cgttggcggt aacaagaaag ggatcttcac tcgcgaccgc aaaccgaagt cggcggcttt    1740
tctgctgcaa aaacgctgga ctggcatgaa cttcggtgaa aaaccgcagc agggaggcaa    1800
acaatga                                                              1807
```

<210> SEQ ID NO 30
<211> LENGTH: 1331
<212> TYPE: DNA
<213> ORGANISM: Artificial sequence
<220> FEATURE:
<223> OTHER INFORMATION: Synthetic sequence: CMV 35S Promoter based on AF502128

<400> SEQUENCE: 30

```
caatcccaca aaaatctgag cttaacagca cagttgctcc tctcagagca gaatcgggta     60
ttcaacaccc tcatatcaac tactacgttg tgtataacgg tccacatgcc ggtatatacg    120
atgactgggg ttgtacaaag gcggcaacaa acggcgttcc cggagttgca cacaagaaat    180
ttgccactat tacagaggca agagcagcag ctgacgcgta cacaacaagt cagcaaacag    240
acaggttgaa cttcatcccc aaaggagaag ctcaactcaa gcccaagagc tttgctaagg    300
ccctaacaag cccaccaaag caaaaagccc actggctcac gctaggaacc aaaaggccca    360
gcagtgatcc agccccaaaa gagatctcct ttgccccgga gattacaatg gacgatttcc    420
tctatcttta cgatctagga aggaagttcg aaggtgaagt agacgacact atgttcacca    480
ctgataatga aaggttagc ctcttcaatt tcagaaagaa tgctgaccca cagatggtta     540
gagaggccta cgcagcaggt ctcatcaaga cgatctaccc gagtaacaat ctccaggaga    600
tcaaatacct tcccaagaag gttaaagatg cagtcaaaag attcaggact aattgcatca    660
agaacacaga gaaagacata tttctcaaga tcagaagtac tattccagta tggacgattc    720
aaggcttgct tcataaacca aggcaagtaa tagagattgg agtctctaaa aaggtagttc    780
ctactgaatc taaggccatg catggagtct aagattcaaa tcgaggatct aacagaactc    840
gccgtgaaga ctggcgaaca gttcatacag agtcttttac gactcaatga caagaagaaa    900
atcttcgtca acatggtgga gcacgacact ctggtctact ccaaaaatgt caaagataca    960
gtctcagaag accaaagggc tattgagact tttcaacaaa ggataatttc gggaaacctc   1020
ctcggattcc attgcccagc tatctgtcac ttcatcgaaa ggacagtaga aaggaaggt    1080 ggctcctaca aatgccatca ttgcgataaa ggaaaggcta tcattcaaga tctctctgcc   1140
gacagtggtc ccaaagatgg acccccaccc acgaggagca tcgtggaaaa agaagacgtt   1200
ccaaccacgt cttcaaagca agtggattga tgtgacatct ccactgacgt aagggatgac   1260
gcacaatccc actatccttc gcaagaccct tcctctatat aaggaagttc atttcatttg   1320
gagaggacac g                                                        1331
```

<210> SEQ ID NO 31
<211> LENGTH: 264

```
<212> TYPE: DNA
<213> ORGANISM: Artificial sequence
<220> FEATURE:
<223> OTHER INFORMATION: Synthetic sequence: nos terminator fragment
      based on GenBank accession EU048864

<400> SEQUENCE: 31
gtcaagcaga tcgttcaaac atttggcaat aaagtttctt aagattgaat cctgttgccg    60
gtcttgcgat gattatcata taatttctgt tgaattacgt gaagcatgta ataattaaca   120
tgtaatgcat gacgttattt atgagatggg tttttatgat tagagtcccg caattataca   180
tttaatacgc gatagaaaac aaaatatagc gcgcaaacta ggataaatta tcgcgcgcgg   240
tgtcatctat gttactagat cgac                                         264

<210> SEQ ID NO 32
<211> LENGTH: 21
<212> TYPE: DNA
<213> ORGANISM: Artificial sequence
<220> FEATURE:
<223> OTHER INFORMATION: Synthetic oligonucleotide primer AS252

<400> SEQUENCE: 32
tgtactccga tgacgtggct t                                             21

<210> SEQ ID NO 33
<211> LENGTH: 20
<212> TYPE: DNA
<213> ORGANISM: Artificial sequence
<220> FEATURE:
<223> OTHER INFORMATION: Synthetic oligonucleotide primer AS253

<400> SEQUENCE: 33
ttcaggaagt ttcccgctca                                               20

<210> SEQ ID NO 34
<211> LENGTH: 200
<212> TYPE: DNA
<213> ORGANISM: Beet curly top virus

<400> SEQUENCE: 34
tgtactccga tgacgtggct tagcatatta acatatctat tggagtattg gagtattata    60
tatattagta caactttcat aagggccatc cgttataata ttaccggatg ccccgaaaaa   120
aatgggcacc caatcaaaac gtgacacgtg gaaggggact gttgaatgat gtgacgtttt   180
tgagcgggaa acttcctgaa                                              200

<210> SEQ ID NO 35
<211> LENGTH: 22
<212> TYPE: DNA
<213> ORGANISM: Artificial sequence
<220> FEATURE:
<223> OTHER INFORMATION: Synthetic oligonucleotide primer AS150

<400> SEQUENCE: 35
aggagtgtca gttaattaaa ga                                            22

<210> SEQ ID NO 36
<211> LENGTH: 19
<212> TYPE: DNA
<213> ORGANISM: Artificial sequence
<220> FEATURE:
<223> OTHER INFORMATION: Synthetic oligonucleotide primer AS151

<400> SEQUENCE: 36
```

```
gtcgactgta tactggacg                                              19
```

<210> SEQ ID NO 37
<211> LENGTH: 244
<212> TYPE: DNA
<213> ORGANISM: Zea mays

<400> SEQUENCE: 37

```
gagtgtcagt taattaaaga gtgtcggggc cgacactctt aatcgaagta aaagtgtggg   60
ttttgctgca ccgacactct aatttaaga gtgtcgggt cccgatgaaa ccgacgcttt  120
taatttaaga gtgtgggttt ttccacaccg acactcttat gaatgttacc ctaaattccc  180
caatcctatt ctacagccgt cgtgcttctt ctctcctttc tccctgcccg ccgtccagta  240
taca                                                              244
```

<210> SEQ ID NO 38
<211> LENGTH: 20
<212> TYPE: DNA
<213> ORGANISM: Artificial sequence
<220> FEATURE:
<223> OTHER INFORMATION: Synthetic oligonucleotide primer AS152

<400> SEQUENCE: 38

```
agtgtcggcc aaaaccccac                                             20
```

<210> SEQ ID NO 39
<211> LENGTH: 20
<212> TYPE: DNA
<213> ORGANISM: Artificial sequence
<220> FEATURE:
<223> OTHER INFORMATION: Synthetic oligonucleotide primer AS153

<400> SEQUENCE: 39

```
cacactctta tatgcgccag                                             20
```

<210> SEQ ID NO 40
<211> LENGTH: 260
<212> TYPE: DNA
<213> ORGANISM: Zea mays

<400> SEQUENCE: 40

```
ccactcttat atgcgcccag gtagcttact gatgtgcgcg cagtaagagt gacggccacg   60
gtactggccg acacttttaa cataagagtg tcggttgctt gttgaaccga cacttttaac  120
ataagagcgt cggtccccac acttctatac gaataagagc gtccatttta gagtgacggc  180
taagagtgtc ggtcaaccga cactcttata cttagagtgt cggcttattt cagtaagagt  240
gtggggtttt ggccgacact                                             260
```

<210> SEQ ID NO 41
<211> LENGTH: 20
<212> TYPE: DNA
<213> ORGANISM: Artificial sequence
<220> FEATURE:
<223> OTHER INFORMATION: Synthetic oligonucleotide primer AS866

<400> SEQUENCE: 41

```
ctgcgtttcg atgcggtcac                                             20
```

<210> SEQ ID NO 42
<211> LENGTH: 21
<212> TYPE: DNA

<213> ORGANISM: Artificial sequence
<220> FEATURE:
<223> OTHER INFORMATION: Synthetic oligonucleotide primer AS867

<400> SEQUENCE: 42
accaatgcct aaagagaggt t                                              21

<210> SEQ ID NO 43
<211> LENGTH: 837
<212> TYPE: DNA
<213> ORGANISM: Escherichia coli

<400> SEQUENCE: 43
ctgcgtttcg atgcggtcac tcattacggc aaagtgtggg tcaataatca ggaagtgatg      60
gagcatcagg gcggctatac gccatttgaa gccgatgtca cgccgtatgt tattgccggg     120
aaaagtgtac gtatcaccgt ttgtgtgaac aacgaactga actggcagac tatcccgccg     180
ggaatggtga ttaccgacga aaacggcaag aaaaagcagt cttacttcca tgatttcttt     240
aactatgccg gaatccatcg cagcgtaatg ctctacacca cgccgaacac ctgggtggac     300
gatatcaccg tggtgacgca tgtcgcgcaa gactgtaacc acgcgtctgt tgactggcag     360
gtggtggcca atggtgatgt cagcgttgaa ctgcgtgatg cggatcaaca ggtggttgca     420
actggacaag gcactagcgg gactttgcaa gtggtgaatc cgcacctctg caaccgggt     480 gaaggttatc tctatgaact gtgcgtcaca gccaaaagcc agacagagtg tgatatctac     540
ccgcttcgcg tcggcatccg gtcagtggca gtgaagggcg aacagttcct gattaaccac     600
aaaccgttct actttactgg ctttggtcgt catgaagatg cggacttgcg tggcaaagga     660
ttcgataacg tgctgatggt gcacgaccac gcattaatgg actggattgg ggccaactcc     720
taccgtacct cgcattaccc ttacgctgaa gagatgctcg actgggcaga tgaacatggc     780
atcgtggtga ttgatgaaac tgctgctgtc ggctttaacc tctctttagg cattggt        837

<210> SEQ ID NO 44
<211> LENGTH: 33
<212> TYPE: DNA
<213> ORGANISM: Artificial sequence
<220> FEATURE:
<223> OTHER INFORMATION: Synthetic oligonucleotide primer AS803

<400> SEQUENCE: 44
gcggctgcag ggcggcggca acaacaacaa caa                                  33

<210> SEQ ID NO 45
<211> LENGTH: 48
<212> TYPE: DNA
<213> ORGANISM: Artificial sequence
<220> FEATURE:
<223> OTHER INFORMATION: Synthetic oligonucleotide primer AS804

<400> SEQUENCE: 45
atctgtacca atcatacgac gagagacttg tcctgtgatt gctacaag                  48

<210> SEQ ID NO 46
<211> LENGTH: 48
<212> TYPE: DNA
<213> ORGANISM: Artificial sequence
<220> FEATURE:
<223> OTHER INFORMATION: Synthetic oligonucleotide primer AS805

<400> SEQUENCE: 46
cttgtagcaa tcacaggaca agtctctcgt cgtatgattg gtacagat                  48

<210> SEQ ID NO 47
<211> LENGTH: 34
<212> TYPE: DNA
<213> ORGANISM: Artificial sequence
<220> FEATURE:
<223> OTHER INFORMATION: Synthetic oligonucleotide primer AS806

<400> SEQUENCE: 47
accatctaga ccaatctcag ccgagtcaat atca                                34

<210> SEQ ID NO 48
<211> LENGTH: 1202
<212> TYPE: DNA
<213> ORGANISM: Artificial sequence
<220> FEATURE:
<223> OTHER INFORMATION: Synthetic sequence: ALS mutagenesis sequence of
      Arabidopsis (ALS-M)

<400> SEQUENCE: 48
gcggcggcaa caacaacaac aacaacatct tcttcgatct ccttctccac caaaccatct     60
ccttcctcct ccaaatcacc attaccaatc tccagattct ccctcccatt ctccctaaac    120
cccaacaaat catcctcctc ctcccgccgc cgcggtatca aatccagctc tccctcctcc    180
atctccgccg tgctcaacac aaccaccaat gtcacaacca ctccctctcc aaccaaacct    240
accaaacccg aaacattcat ctcccgattc gctccagatc aaccccgcaa aggcgctgat    300
atcctcgtcg aagctttaga acgtcaaggc gtagaaaccg tattcgctta ccctggaggt    360
gcatcaatgg agattcacca agccttaacc cgctcttcct caatccgtaa cgtccttcct    420
cgtcacgaac aaggaggtgt attcgcagca gaaggatacg ctcgatcctc aggtaaacca    480
ggtatctgta tagccacttc aggtcccgga gctacaaatc tcgttagcgg attagccgat    540
gcgttgttag atagtgttcc tcttgtagca atcacaggac aagtctctcg tcgtatgatt    600
ggtacagatg cgtttcaaga gactccgatt gttgaggtaa cgcgttcgat tacgaagcat    660
aactatcttg tgatggatgt tgaagatatc cctaggatta ttgaggaagc tttctttttta    720 gctacttctg gtagacctgg acctgttttg gttgatgttc ctaaagatat tcaacaacag    780
cttgcgattc ctaattggga acaggctatg agattacctg gttatatgtc taggatgcct    840
aaacctccgg aagattctca tttggagcag attgttaggt tgatttctga gtctaagaag    900
cctgtgttgt atgttggtgg tggttgtttg aattctagcg atgaattggg taggtttgtt    960
gagcttacgg ggatccctgt tgcgagtacg ttgatggggc tgggatctta tccttgtgat   1020
gatgagttgt cgttacatat gcttggaatg catgggactg tgtatgcaaa ttacgctgtg   1080
gagcatagtg atttgttgtt ggcgtttggg gtaaggtttg atgatcgtgt cacgggtaag   1140
cttgaggctt ttgctagtag ggctaagatt gttcatattg atattgactc ggctgagatt   1200
gg                                                                 1202

<210> SEQ ID NO 49
<211> LENGTH: 56
<212> TYPE: DNA
<213> ORGANISM: Artificial sequence
<220> FEATURE:
<223> OTHER INFORMATION: Synthetic oligonucleotide primer AS690

<400> SEQUENCE: 49
ctcgagactt tccattttta gtaactacca ccatgttacg tcctgtagaa acccca         56

```
<210> SEQ ID NO 50
<211> LENGTH: 25
<212> TYPE: DNA
<213> ORGANISM: Artificial sequence
<220> FEATURE:
<223> OTHER INFORMATION: Synthetic oligonucleotide primer AS300

<400> SEQUENCE: 50
aattgtttgc ctccctgctg gcctt                                          25

<210> SEQ ID NO 51
<211> LENGTH: 20
<212> TYPE: DNA
<213> ORGANISM: Artificial sequence
<220> FEATURE:
<223> OTHER INFORMATION: Synthetic sequence: AP3 domain

<400> SEQUENCE: 51
agttactaaa aatggaaagt                                                20

<210> SEQ ID NO 52
<211> LENGTH: 25
<212> TYPE: DNA
<213> ORGANISM: Artificial sequence
<220> FEATURE:
<223> OTHER INFORMATION: Synthetic oligonucleotide primer AS429

<400> SEQUENCE: 52
ggctcgagat gggaaggggt agggt                                          25

<210> SEQ ID NO 53
<211> LENGTH: 25
<212> TYPE: DNA
<213> ORGANISM: Artificial sequence
<220> FEATURE:
<223> OTHER INFORMATION: Synthetic oligonucleotide primer AS430

<400> SEQUENCE: 53
catcgatttc ggcgtaagag tacct                                          25

<210> SEQ ID NO 54
<211> LENGTH: 231
<212> TYPE: DNA
<213> ORGANISM: Arabidopsis thaliana

<400> SEQUENCE: 54
atgggaaggg gtagggttca attgaagagg atagagaaca agatcaatag acaagtgaca     60
ttctcgaaaa gaagagctgg tctttt gaag aaagctcatg agatctctgt tctctgtgat    120
gctgaagttg ctcttgttgt cttctcccat aagggaaaac tcttcgaata ctccactgat    180
tcttgtatgg agaagatact tgaacgctat gagaggtact cttacgccga a             231

<210> SEQ ID NO 55
<211> LENGTH: 27
<212> TYPE: DNA
<213> ORGANISM: Artificial sequence
<220> FEATURE:
<223> OTHER INFORMATION: Synthetic oligonucleotide primer AS912

<400> SEQUENCE: 55
gccgcggctt tattaccgtg aatatta                                        27

<210> SEQ ID NO 56
<211> LENGTH: 30
<212> TYPE: DNA
```

```
<213> ORGANISM: Artificial sequence
<220> FEATURE:
<223> OTHER INFORMATION: Synthetic oligonucleotide primer AS913

<400> SEQUENCE: 56
cgcggccgct ctgataagtg caacctgatt                                          30

<210> SEQ ID NO 57
<211> LENGTH: 349
<212> TYPE: DNA
<213> ORGANISM: Nicotiana tabacum

<400> SEQUENCE: 57
gccgcggctt tattaccgtg aatattattt tggtaagggg tttattccca acaactggta         60
tcagagcaca ggttctgctc gttcactgaa atactattca ctgtcggtag tactatactt        120
ggtgaaaaat aaaaatgtct ggagtaaagt acgaggtagc aaaattcaat ggagataacg        180
gtttctcaac atggcaaaga aggatgagag atctgctcat ccaacaagga ttacacaagg        240
ttctagatgt tgattccaaa aagcctgata ccatgaaagc tgaggattgg gctgacttgg        300
atgaaagagc tgctagtgca atcaggttgc acttatcaga gcggccgcg                    349

<210> SEQ ID NO 58
<211> LENGTH: 32
<212> TYPE: DNA
<213> ORGANISM: Artificial sequence
<220> FEATURE:
<223> OTHER INFORMATION: Synthetic oligonucleotide primer AS885

<400> SEQUENCE: 58
tctcgagaac atgcagcata gagtctcatt tc                                       32

<210> SEQ ID NO 59
<211> LENGTH: 23
<212> TYPE: DNA
<213> ORGANISM: Artificial sequence
<220> FEATURE:
<223> OTHER INFORMATION: Synthetic oligonucleotide primer Tnt-RT-R

<400> SEQUENCE: 59
ctagtttgaa tgcattccga caa                                                 23

<210> SEQ ID NO 60
<211> LENGTH: 1845
<212> TYPE: DNA
<213> ORGANISM: Nicotiana tabacum

<400> SEQUENCE: 60
atgtcagaaa aggtgaagaa tggtataatt cctaactttg ttactattcc ttctacttct         60
aacaatccca caagtgcaga aagtacgacc gacgaggttt ccgagcaggg ggagcaacct        120
ggtgaggtta ttgagcaggg ggagcaactt gatgaaggtg tcgaggaagt ggagcacccc        180
actcagggag aagaacaaca tcaacctctg aggagatcag agaggccaag ggtagagtca        240
cgcaggtacc cttccacaga gtatgtcctc atcagtgatg agggggagcc agaaagtctt        300
aaggaggtgt tgtcccatcc agaaaagaac cagtggatga agctatgca agaagagatg        360 gaatctctcc agaaaaatgg cacatacaag ctggttgaac ttccaaaggg taaaagacca        420
ctcaaatgca aatgggtctt taaactcaag aaagatggag atgcaagct ggtcagatac        480 aaagctcgat tggtggttaa aggcttcgaa cagaagaaag gtattgattt tgacgaaatt        540
ttctcccccg ttgttaaaat gacttctatt cgaacaattt tgagcttagc agctagccta        600
```

```
gatcttgaag tggagcagtt ggatgtgaaa actgcatttc ttcatggaga tttggaagag    660
gagatttata tggagcaacc agaaggattt gaagtagctg aaagaaaca catggtgtgc     720 aaattgaata agagtcttta tggattgaag caggcaccaa ggcagtggta catgaagttt    780
gattcattca tgaaaagtca aacataccta aagacctatt ctgatccatg tgtatacttc    840
aaaagatttt ctgagaataa ctttattata ttgttgttgt atgtggatga catgctaatt    900
gtaggaaaag acaaggggtt gatagcaaag ttgaaaggag atctgtccaa gtcatttgat    960
atgaaggact gggcccagc acaacaaatt ctagggatga agatagttcg agagagaaca    1020
agtagaaagt tgtggctatc tcaggagaag tacattgaac gtgtactaga acgcttcaac    1080
atgaagaatg ctaagccagt cagcacacct cttgctggtc atctaaagtt gagtaaaaag    1140
atgtgtccta caacagtgga agagaaaggg aacatggcta agttccttta ttcttcagca    1200
gtcggaagct tgatgtatgc aatggtatgt actagacctg atattgctca cgcagttggt    1260
gttgtcagca ggtttcttga aaatcctgga aggaacatt gggaagcagt caagtggata    1320
ctcaggtacc tgagaggtac cacgggagat tgtttgtgct ttggaggatc tgatccaatc    1380
ttgaagggct atacagatgc tgatatggca ggtgacattg acaacagaaa atccagtact    1440
ggatatttgt ttacattttc aggggagct atatcatggc agtctaagtt gcaaaagtgc    1500
gttgcacttt caacaactga agcagagtac attgctgcta cagaaactgg caaggagatg    1560
atatggctca agcgattcct tcaagagctt ggattgcatc agaaggagta tgtcgtctat    1620
tgtgacagtc aaagtgcaat agaccttagc aagaactcta tgtaccatgc aaggaccaaa    1680
cacattgatg tgagatatca ttggattcga gaaatggtag atgatgaatc tctaaaagtc    1740
ttgaagattt ctacaaatga gaatcccgca gatatgctga ccaaggtggt accaaggaac    1800
aagttcgagc tatgcaaaga acttgtcgga atgcattcaa actag                   1845
```

<210> SEQ ID NO 61
<211> LENGTH: 29
<212> TYPE: DNA
<213> ORGANISM: Artificial sequence
<220> FEATURE:
<223> OTHER INFORMATION: Synthetic oligonucleotide primer AS1031

<400> SEQUENCE: 61
gcccgggtcc tccaccctcc tccctagat                                        29

<210> SEQ ID NO 62
<211> LENGTH: 31
<212> TYPE: DNA
<213> ORGANISM: Artificial sequence
<220> FEATURE:
<223> OTHER INFORMATION: Synthetic oligonucleotide primer AS1034

<400> SEQUENCE: 62
atcctacgtg ccacttgacc ggttatagca a                                     31

<210> SEQ ID NO 63
<211> LENGTH: 31
<212> TYPE: DNA
<213> ORGANISM: Artificial sequence
<220> FEATURE:
<223> OTHER INFORMATION: Synthetic oligonucleotide primer AS1035

<400> SEQUENCE: 63
cggtcaagtg gcacgtagga tgatcggtac t                                     31

<210> SEQ ID NO 64
<211> LENGTH: 22
<212> TYPE: DNA
<213> ORGANISM: Artificial sequence
<220> FEATURE:
<223> OTHER INFORMATION: Synthetic oligonucleotide primer AS1036

<400> SEQUENCE: 64

```
atctagaacc tggatagcat at                                              22
```

<210> SEQ ID NO 65
<211> LENGTH: 1339
<212> TYPE: DNA
<213> ORGANISM: Artificial sequence
<220> FEATURE:
<223> OTHER INFORMATION: Synthetic sequence: Mutated donor for targeting
      of tobacco endogenous acetolactate synthase (ALS) gene

<400> SEQUENCE: 65

```
gcccgggtcc tccaccctcc tccctagatc caccttccct ttcccccacc accccacaa      60 aaccacccca ccaccctcc acctcacccc cacccacatt cacagccaac gccgtcgttt     120
caccatctcc aatgtcattt ccactaccca aaaagtttcc gagacccaaa aagccgaaac    180
tttcgttccc cgttttgccc ctgacgaacc cagaaagggt tccgacgttc tcgtggaggc    240
cctcgaaaga aaggggtta cggacgtttt tgcgtaccca ggcggcgctt ccctcgagat     300
tcaccaagct ttgacgcgct caagcatcat ccgcaacgtg ctaccacgtc acgagcaggg    360
tggtgtcttc gccgctgagg gttacgcacg cgccaccggc ttccccggcg tttgcattgc    420
cacctccggc cctggcgcca ccaatctcgt cagtggcctc gcggacgccc tactggatag    480
cgtccccatt gttgctataa ccggtcaagt ggcacgtagg atgatcggta ctgatgcttt    540
tcaggaaact ccgattgttg aggtaactag atcgattacc aagcataatt atctcgttat    600
ggacgtagag gatattccta gggttgtacg tgaggctttt tccttgcga atcgggccg      660 gcctggccct gttttgattg atgtacctaa ggatattcag caacaattgg tgatacctga    720
ctgggatcag ccaatgaggt tgcctggtta catgtctagg ttacctaaat tgcccaatga    780
gatgctttta gaacaaattg ttaggcttat ttctgagtca aagaagcctg ttttgtatgt    840 gggggggtggg tgttcgcaat cgagtgagga gttgagacga ttcgtggagc tcaccggtat   900
ccccgtggca agtactttga tgggtcttgg agcttttcca actggggatg agctttccct    960
ttcaatgttg ggtatgcatg gtactgtttta tgctaattat gctgtggaca gtagtgatttt 1020 attgctcgca tttggggtga ggtttgatga tagagttact ggaaagttag aagcttttgc   1080
tagccgagcg aaaattgttc acattgatat tgattcagct gagattggaa agaacaagca   1140
gcctcatgtt tccatttgtg cggatatcaa gttggcgtta caggggtttga attcgatatt   1200 ggagagtaag gaaggtaaac tgaagttgga ttttttctgct tggaggcagg agttgacggt   1260
gcagaaagtg aagtacccgt tgaattttaa aacttttggt gatgctattc ctccgcaata   1320
tgctatccag gttctagat                                                1339
```

<210> SEQ ID NO 66
<211> LENGTH: 28
<212> TYPE: DNA
<213> ORGANISM: Artificial sequence
<220> FEATURE:
<223> OTHER INFORMATION: Synthetic oligonucleotide primer AS1020

<400> SEQUENCE: 66

```
gggtacccccg acgacggagg ttgaggct                                          28
```

<210> SEQ ID NO 67
<211> LENGTH: 28
<212> TYPE: DNA
<213> ORGANISM: Artificial sequence
<220> FEATURE:
<223> OTHER INFORMATION: Synthetic oligonucleotide primer AS1021

<400> SEQUENCE: 67

```
cgaattcatg ggctgcttta gataaatc                                           28
```

<210> SEQ ID NO 68
<211> LENGTH: 28
<212> TYPE: DNA
<213> ORGANISM: Artificial sequence
<220> FEATURE:
<223> OTHER INFORMATION: Synthetic oligonucleotide primer AS1022

<400> SEQUENCE: 68

```
ttctagaccg acgacggagg ttgaggct                                           28
```

<210> SEQ ID NO 69
<211> LENGTH: 28
<212> TYPE: DNA
<213> ORGANISM: Artificial sequence
<220> FEATURE:
<223> OTHER INFORMATION: Synthetic oligonucleotide primer AS1023

<400> SEQUENCE: 69

```
cccgcggatg ggctgcttta gataaatc                                           28
```

<210> SEQ ID NO 70
<211> LENGTH: 255
<212> TYPE: DNA
<213> ORGANISM: Maize streak virus

<400> SEQUENCE: 70

```
ccgacgacgg aggttgaggc tgagggatgg cagactggga gctccaaact ctatagtata        60
cccgtgcgcc ttcgaaatcc gccgctccct tgtcttatag tggttgcaaa tgggccggac       120
cgggccggcc cagcaggaaa agaaggcgcg cactaatatt accgcgcctt cttttcctgc       180
gagggccccgg tagggcccga gcgatttgat gtaaagtttg gtcctgcttt gtatgattta      240
tctaaagcag cccat                                                        255
```

<210> SEQ ID NO 71
<211> LENGTH: 29
<212> TYPE: DNA
<213> ORGANISM: Artificial sequence
<220> FEATURE:
<223> OTHER INFORMATION: Synthetic oligonucleotide primer AS965

<400> SEQUENCE: 71

```
ggaattcatg aatgaatcgc acttgttag                                          29
```

<210> SEQ ID NO 72
<211> LENGTH: 32
<212> TYPE: DNA
<213> ORGANISM: Artificial sequence
<220> FEATURE:
<223> OTHER INFORMATION: Synthetic oligonucleotide primer AS966

<400> SEQUENCE: 72

```
actaatatta cgagggcccg gtagggcccg ag                                      32
```

-continued

<210> SEQ ID NO 73
<211> LENGTH: 32
<212> TYPE: DNA
<213> ORGANISM: Artificial sequence
<220> FEATURE:
<223> OTHER INFORMATION: Synthetic oligonucleotide primer AS967

<400> SEQUENCE: 73
accgggccct cgtaatatta gtgcgcgcct tc                           32

<210> SEQ ID NO 74
<211> LENGTH: 29
<212> TYPE: DNA
<213> ORGANISM: Artificial sequence
<220> FEATURE:
<223> OTHER INFORMATION: Synthetic oligonucleotide primer AS968

<400> SEQUENCE: 74
cggtaccgag tgttggcaac cagtaatga                              29

<210> SEQ ID NO 75
<211> LENGTH: 34
<212> TYPE: DNA
<213> ORGANISM: Artificial sequence
<220> FEATURE:
<223> OTHER INFORMATION: Synthetic oligonucleotide primer AS1039

<400> SEQUENCE: 75
gtgtttgaga gaggtatgta aatatgaact gtat                        34

<210> SEQ ID NO 76
<211> LENGTH: 34
<212> TYPE: DNA
<213> ORGANISM: Artificial sequence
<220> FEATURE:
<223> OTHER INFORMATION: Synthetic oligonucleotide primer AS1040

<400> SEQUENCE: 76
catatttaca tacctctctc aaacacagcc agag                        34

<210> SEQ ID NO 77
<211> LENGTH: 34
<212> TYPE: DNA
<213> ORGANISM: Artificial sequence
<220> FEATURE:
<223> OTHER INFORMATION: Synthetic oligonucleotide primer AS1041

<400> SEQUENCE: 77
gtataacttg caggtacttt cattcctagg aagt                        34

<210> SEQ ID NO 78
<211> LENGTH: 34
<212> TYPE: DNA
<213> ORGANISM: Artificial sequence
<220> FEATURE:
<223> OTHER INFORMATION: Synthetic oligonucleotide primer AS1042

<400> SEQUENCE: 78
ggaatgaaag tacctgcaag ttatacgatc agga                        34

<210> SEQ ID NO 79
<211> LENGTH: 1754
<212> TYPE: DNA
<213> ORGANISM: Artificial sequence
<220> FEATURE:

<223> OTHER INFORMATION: Synthetic sequence

<400> SEQUENCE: 79

```
ggaattcatg aatgaatcgc acttgttagg caatttatag tgaccgggac cggattcttt      60
agaatgggct gctttagata aatcatacaa agcaggacca aactttacat caaatcgctc     120
gggccctacc gggccctcgt aatattagtg cgcgccttct tttcctgctg ggccggcccg     180
gtccggccca tttgcaacca ctataagaca agggagcggc ggatttcgaa ggcgcacggg     240
tatactatag agtttggagc tcccagtctg ccatccctca gcctcaacct ccgtcgtcgg     300
caatggcctc ctcctcatcc aaccgtcagt tctcacaccg gaacgctaac acgttcctaa     360
cctatccaaa gtgtccagaa atcctgaaaa tcgcctgtca gatgatctgg gagctcgttg     420
ttcgttggat tcccaaatac attctatgtg cccgagaggc acataaagat ggaagtttgc     480
atttacatgc attgcttcag acagagaagc cggtaaggat atctgactca aggttctttg     540
atataaatgg gtttcaccca atattcaga gtgccaagtc agtaaacagg gtgagggatt       600
acattctcaa ggaacctctg gctgtgtttg agagaggtat gtaaatatga actgtatatg     660
acaagtctca ctgccatggg ttacgtttca atcaagtcca caagtgataa atattgtcct     720
gatcgtataa cttgcaggta cttttcattcc taggaagtcc cccttcctag gaaaatctga    780
ttcagaggta aaggaaaaaa agccttctaa agatgaaata atgcgagaca ttatttcaca     840
cgctacttcc aaagaagagt acctctccat gatccagaaa gagcttccct ttgattggtc     900
cacaaaattg cagtatttg aatactctgc aaataagctt tttcctgaga ttcaggaaga       960
gttcaccaat cctcatccac cctcatcacc tgatttactt tgtaatgagt caatcaatga    1020
ttggctccag cctaacatct tccaggttag tcccgaagct acatgctcc ttcaacctac     1080
ctgttatacc ctcgaggatg caatttctga cctccaatgg atggattctg tatccagtca    1140
tcagatgaaa gatcaagaaa gcagagcctc tacatcgtcg gcccaacaag aaccggaaaa    1200
tctacttggg ccagaagcct agggggttcat aattactggc aaaataatgt tgattggtct   1260
tcatacaacg aagacgcaat ctataacatc gtagatgata ttccgtttaa attctgtcct    1320
tgttggaaac agttagttgg ctgtcagagg gatttcattg taaacccccaa gtatggtaaa   1380
aagaaaaagg tgcagaagaa gtctaagcct acaataatcc tcgccaactc ggatgaagat    1440
tggatgaagg aaatgactcc agggcagctg gagtatttcg aggcaaactg catcatttac    1500
attatgtcgc cgggggagaa atggtattct cccctgagc tgcctcctac ggaggcagta     1560
cattcagata gatcttgatt tttcgatgtt ctgcccgccg agcaccaccc ttagccgccc    1620
gccgactacc cccctgtatt gattgtgtgt gttttcgtg ccatcgcacg acatattaat      1680
gtaagctttc agcattcatc agatataata aaaacggcgt tttattcatt actggttgcc    1740
aacactcggt accg                                                      1754
```

<210> SEQ ID NO 80
<211> LENGTH: 29
<212> TYPE: DNA
<213> ORGANISM: Artificial sequence
<220> FEATURE:
<223> OTHER INFORMATION: Synthetic oligonucleotide primer AS1011

<400> SEQUENCE: 80

```
gctgcagatc gtggggcagg acgagatga                                        29
```

<210> SEQ ID NO 81
<211> LENGTH: 29

```
<212> TYPE: DNA
<213> ORGANISM: Artificial sequence
<220> FEATURE:
<223> OTHER INFORMATION: Synthetic oligonucleotide primer AS1012

<400> SEQUENCE: 81
ggcgcgccgt gggagatgga gataccctc                                     29

<210> SEQ ID NO 82
<211> LENGTH: 29
<212> TYPE: DNA
<213> ORGANISM: Artificial sequence
<220> FEATURE:
<223> OTHER INFORMATION: Synthetic oligonucleotide primer AS1013

<400> SEQUENCE: 82
ggcgcgcccc ctgctcggtt catcctcat                                     29

<210> SEQ ID NO 83
<211> LENGTH: 29
<212> TYPE: DNA
<213> ORGANISM: Artificial sequence
<220> FEATURE:
<223> OTHER INFORMATION: Synthetic oligonucleotide primer AS1014

<400> SEQUENCE: 83
gactagtaag acttcataaa acttctcaa                                     29

<210> SEQ ID NO 84
<211> LENGTH: 1015
<212> TYPE: DNA
<213> ORGANISM: Artificial sequence
<220> FEATURE:
<223> OTHER INFORMATION: Synthetic sequence: Fragment of magnesium
      chelatase gene from rice with introduced premature stop codon

<400> SEQUENCE: 84
gctgcagatc gtggggcagg acagatgaa gctgtgcctg ctgctcaacg tcatcgaccc     60
taagatcggc ggtgtcatga tcatgggaga ccgtggcacc ggcaaatcca ccaccgtccg   120
ctcgctcgtc gacctgctcc cggatatccg cgtcgttgtt ggcgacccctt tcaattccga   180 ccctgacgat cccgaggtca tgggccctga ggtccgggaa cgcgtgctgg agggtgagaa   240
gcttcctgtt gtcacggcca agatcaccat ggtagatctt ccccttggtg ccactgagga   300
tagagtctgt ggcaccattg atattgagaa ggcgctcacc gatggtgtca aggcgttcga   360
gcctggtttg cttgccaagg ccaacagggg gattctttat gtggatgagg tcaatttgtt   420
ggatgaccat ctagtagatg tgcttctgga ttctgctgcg tcaggatgga acaccgtgga   480 gagagaggt atctccatct cccacggcgc gccccctgct cggttcatcc tcattgggtc   540
tggtaacccc gaggaagggg agctccggcc acagctgctt gaccggtttg gcatgcacgc   600
gcaggttggt actgtcaggg atgctgaact cagggtgaaa attgttgaag agagagctcg   660
gttcgacagg gatccaaagg cgttccgtga gtcctacttg gaggaacaag acaagctcca   720
gcagcagatt tcatctgctc ggagtaacct tggtgctgtg cagattgacc atgatcttcg   780
tgttaagatt tctaaagtgt gtgcagagtt gaatgttgat ggattaagag gggacattgt   840
gactaacagg gctgccaagg cgttggcagc actcaaaggc agggacactg tcactgtaga   900
ggacattgcc actgttatcc ccaactgctt gaggcatcgg cttcggaagg acccacttga   960
atcaattgac tcaggattgc tcgtggttga gaagttttat gaagtcttac tagtg        1015
```

GENE TARGETING IN PLANTS USING A CHIMERIC MULTI DOMAIN RECOMBINATION PROTEIN

CROSS REFERENCE TO RELATED APPLICATIONS

This application is a National Stage of International Application No. PCT/GB2010/000111 filed Jan. 25, 2010, claiming priority based on Great Britain Patent Application No. 0901249.3 filed Jan. 26, 2009, the contents of all of which are incorporated herein by reference in their entirety.

The present invention relates to a method for altering a plant genotype by introducing genetic alterations to a plant cell genome, plant cells comprising genetically altered nuclear DNA, nucleic acid sequences and polypeptides generated as a result of introduction of genetic changes and whole plants and/or plant parts. In particular, the method relates to a more efficient method for introducing mutations or deletions in nucleic acid sequences of interest in situ, the repair of nucleic acid sequences in plant cells, the introduction of novel nucleic acids into chromosomal sites of interest and the generation of novel domains within genes of interest in a targeted manner, the genetic material required therefor, such as DNA and RNA, vectors, host cells, plant cells comprising genetically modified nuclear genomes, plants derived from said plant cells and uses thereof.

A disadvantage of prior art nuclear transformation methods is that the efficiency of gene targeting for repair, alteration of function purposes, or for the introduction of polynucleotides of interest at specific sites within the genome tends to be low. Furthermore, the accurate targeting of nuclear genes within populations of cells is inefficient. As a consequence, the targeting of genes within the nuclear genome in cells is patchy, with a low percentage uptake of introduced genetic material at the correct site or locus. As a further consequence, the efficiency of gene repair at specific sites within the genome, of the introduction of desired alterations, or even of the introduction of genes of interest, is low. A further disadvantage of prior art methods is that the delivery of genetic information into the genome tends to be erratic since the delivery mechanisms employed rely on chance for the successful delivery of genetic information, such as DNA, into the nuclear genome at desired sites. The ability to efficiently target genes of interest within the plant cell needs to be improved such that better plant varieties may be created with a higher degree of certainty and with a higher level of gene targeting performance. As such, prior art processes appear to lack a truly efficient means of gene targeting. These and other disadvantages of prior art gene targeting technology will become apparent from the description.

The present inventors have developed a robust and reproducible technique for site-specific modifications within the plant nuclear genome. The essence of gene targeting as developed herein lies in the efficient placing of donor polynucleotide sequences, such as native DNA or cDNA of choice, alongside the DNA of a targeted site within a gene or a plurality of gene sequences, and by inducing recombination between the donor polynucleotide sequence or donor polynucleotide sequences and the target site or sites, efficient transformation events are able to occur at a high efficiency. The gene targeting technique makes use of two components: (1) a multi-domain recombination protein (MDRP); and (2) a donor amplification vector system (DAV).

The MDRP of the invention possesses at least the first two of the following functionalities:

(i) it is capable of binding to a donor polynucleotide, such as an introduced native DNA or a cDNA;
(ii) it is capable of binding to a chromosomal polynucleotide;
(iii) it is capable of locating specific target nucleic acid sequences, such as DNA coding for a native gene or a part thereof in the nuclear genome; and
(iv) it is capable of initiating the annealing of homologous polynucleotides, such as DNA sequences, between target and donor.

The DAV is a molecular tool for the amplification of a donor fragment or of donor fragments of polynucleotide, such as those derived from native or cDNA sequences of interest in a plant cell, and is capable of providing a permanent and abundant supply of donor polynucleotide sequences, such as cDNA or native DNA molecules, for efficient gene targeting.

According to a first aspect of the invention there is provided an isolated polynucleotide sequence that encodes for a multi domain recombination protein (MDRP) that comprises
i) a donor DNA-Binding domain; and
ii) a chromosomal binding domain.

The donor DNA-binding domain or domains may be selected from the CACTA super-family of transposable elements, especially of those transposable elements found in eukaryotes such as plants, for example, the maize transposable element En/Spm (Pereira et al., (1986) *EMBO J* 1986, 5:835-841), Tpn1 from *Ipomoea nil* (Inagaki et al., (1994) *Plant Cell*, 6:375-383); Tdc1 from *Daucus carota* (Ozeki et al., (1997) *Mol Gen Genet*, 254:407-416); PsI from *Petunia hybrida* (Snowden & Napoli (1998) *Plant J*, 14:43-54); Candystripe1 (Cs1) from *Sorghum bicolor* (Chopra et al., (1999) *Proc Natl Acad Sci*, 96:15330-15335); Atenspm1 (or CAC1) from *Arabidopsis thaliana* (Miura A, et al., (2001) *Nature*, 411:212-214); Tpo1 from *Lolium perenne* (Langdon et al., (2003) *Genetics*, 163:1097-1108); and TamRSA1 of *A. majus* (Roccaro et al., (2007) *Mol Genet Genomics*, 278: 243-254), and DNA binding domains from bacterial restriction endonucleases, such as EcoRV restrictase. Suitable DNA binding domains may be selected from the whole tnpA protein of En/Spm, or selected fragments thereof, for example the polypeptide sequence between positions 122 to 427 of tnpA.

DNA-binding domains for use in the present invention typically have a strong binding affinity for so-called 'sub-terminal' regions. Suitable sub-terminal regions for use in methods of the present invention comprise repetitive short motifs that are typically from about 7 to about 25 nucleotide base pairs in length. Such motifs are typically located at both termini of a CACTA transposable DNA element, such as, for example, the En/Spm transposon. The repetitive motifs may be located at either terminus or both termini of the CACTA family of transposable element nucleic acid sequences. Members of the CACTA family of transposable element nucleic acid sequences includeEn/Spm from maize (Pereira et al., (1986) *EMBO J* 1986, 5:835-841), Tpn1 from *Ipomoea nil* (Inagaki et al., (1994) *Plant Cell*, 6:375-383); Tdc1 from *Daucus carota* (Ozeki et al., (1997) *Mol Gen Genet*, 254:407-416); PsI from *Petunia hybrida* (Snowden & Napoli (1998) *Plant J*, 14:43-54); Candystripe1 (Cs1) from *Sorghum bicolor* (Chopra et al., (1999) *Proc Natl Acad Sci*, 96:15330-15335); Atenspm1 (or CAC1) from *Arabidopsis thaliana* (Miura A, et al., (2001) *Nature*, 411:212-214); Tpo1 from *Lolium perenne* (Langdon et al., (2003) *Genetics*, 163:1097-1108); and TamRSA1 of *A. majus* (Roccaro et al., (2007) *Mol Genet Genomics*, 278:243-254). Suitable sub-terminal sequences for use in the invention include the 6 hyper-reactive 12 bp motifs at the left sub-terminal region (STR1) and the 8 hyper-reactive 12 bp motifs at the right sub-terminal region (STR2) of the En/Spm DNA sequence polynucleotide sequence. The sub-terminal sequences may be used as flanking regions for the donor fragment in the donor amplification vector of the invention.

Transposable element proteins, such as tnpA, typically have a second function, that of mediating the association of the sub-terminal regions with chromosomal DNA sequences, and as a result may also possess a chromosomal DNA binding functionality, such as in the case of the tnpA protein sequence, provided herein. Other transposable element proteins may lack such chromosomal DNA binding functionality, and this type of functionality may be built into them by fusing sequences having such functionality with transposable elements lacking functionality, using conventional procedures in the art.

Thus, the chromosomal binding domain (CBD) may also be selected from mobile genetic elements such as Spm from maize (Pereira et al., (1986) *EMBO J* 1986, 5:835-841), Tpn1 from *Ipomoea nil* (Inagaki et al., (1994) *Plant Cell*, 6:375-383); Tdc1 from *Daucus carota* (Ozeki et al., (1997) *Mol Gen Genet*, 254:407-416); PsI from *Petunia hybrida* (Snowden & Napoli (1998) Plant J, 14:43-54); Candystripe1 (Cs1) from *Sorghum bicolor* (Chopra et al., (1999) *Proc Natl Acad Sci*, 96:15330-15335); Atenspm1 (or CAC1) from *Arabidopsis thaliana* (Miura A, et al., (2001) *Nature*, 411: 212-214); Tpo1 from *Lolium perenne* (Langdon et al., (2003) *Genetics*, 163:1097-1108); and TamRSA1 of *A. majus* (Roccaro et al., (2007) *Mol Genet Genomics*, 278: 243-254) and DNA binding domains from bacterial restriction endonucleases, such as the well characterised EcoRV restrictase.

Preferably, the isolated polynucleotide sequence encoding the MDRP further comprises a third domain that is a chromosomal target binding domain and is typically designed according to the sequence of the target site gene or gene fragment of interest. The target binding domain of the MDRP may be selected from gene specific DNA-binding proteins such as transcription factors or MADS domain proteins as described in, for example, Pellegrini et al., (1995) Nature, 376, 490-498; Schwechheimer et al., (1998) Ann Review Plant Physiol Plant Mol Biol., 49, 127-150), zinc-finger nucleases (ZFN) or meganuclease (MN) binding domains (Bibikova et al., (2003) Science, 300, 764-766; Epinat et al., (2003) Nuc Acid Res, 31, 2952-2962).

In a further preferment, the isolated polynucleotide sequence encoding a MDRP comprises a fourth domain that is a recombination inducing domain (RID). Homologous DNA pairing can be promoted by short peptide domains from DNA repair proteins. Typically, such short peptide domains are of about 15 to about 50 amino acid residues in length and as an example of a short peptide of use in the invention there is provided the 20 amino acid domain derived from the recA protein of *E. coli*. These short domains may be fused to the DNA binding protein, for example, tnpA as provided herein, resulting in tnpAA, and used as a RID of MDRP. The RID may also be selected from well characterised proteins involved in the induction of homologous recombination as described by Symington, (2002) Microbiology and Molecular Biology Reviews, 66, 630-670. Such proteins include rad 51 and rad 52 proteins that are found in plants, fungi, algae and animals.

Naturally, the man skilled in the art will appreciate that MDRP polynucleotide sequences may be comprised of genomic DNA or cDNA sequences or a combination of both.

The polynucleotide sequence encoding for the MRDP protein is preferably delivered on one vector as outlined herein. However, the man skilled in the art will appreciate that separate polynucleotide sequences encoding for different domains of the MDRP protein of the invention, may be delivered on more than one vector.

In a further aspect of the invention there is provided a method of transforming a plant cell that comprises:
1) introducing into the said plant cell a nucleic acid sequence that comprises a plant nuclear promoter operably linked to a first nucleic acid sequence that comprises a polynucleotide sequence encoding a MDRP; and
2) introducing into the said plant cell a second nucleic acid sequence that comprises
   i) a donor nucleic acid sequence;
   ii) at least two flanking sequences located adjacent to each end of the donor polynucleotide sequence forming left and right borders thereto.

Preferably, the second nucleic acid sequence further comprises a viral origin of replication located 5' and 3' to each of the said left and right borders. The viral origin of replication may be selected from Mastreviruses (such as maize streak virus (MSV), wheat dwarf virus (WDV)), Curtoviruses (such as beet curly top virus (BCTV), Begomoviruses (such as bean golden mosaic virus (BGMV), tomato golden mosaic virus (TGMV), squash leaf curl virus (SqLCV) and tomato yellow leaf curl virus (TYLCV) (Gutierrez, (1999) CMLS, Cell. Mol. Life. Sci. 56 (1999) 313-329).

The plant nuclear promoter may be selected from any suitable promoters, such as constitutive, inducible, tissue specific, or other promoters as indicated herein.

The term "inducible" as applied to a promoter is well understood by those skilled in the art. In essence, expression under the control of an inducible promoter is "switched on" or increased in response to an applied stimulus (which may be generated within a cell or provided exogenously). The nature of the stimulus varies between promoters. Some inducible promoters cause little or undetectable levels of expression (or no expression) in the absence of the appropriate stimulus. Other inducible promoters cause detectable constitutive expression in the absence of the stimulus. Whatever the level of expression is in the absence of the stimulus, expression from any inducible promoter is increased in the presence of the correct stimulus. The preferable situation is where the level of expression increases upon application of the relevant stimulus by an amount effective to alter a phenotypic characteristic. Thus an inducible (or "switchable") promoter may be used which causes a basic level of expression in the absence of the stimulus which level is too low to bring about a desired phenotype (and may in fact be zero). Upon application of the stimulus, expression is increased (or switched on) to a level, which brings about the desired phenotype. One example of an inducible promoter is the ethanol inducible gene switch disclosed in Caddick et al (1998) Nature Biotechnology 16: 177-180. A number of inducible promoters are known in the art.

Chemically regulated promoters can be used to modulate the expression of a gene or a polynucleotide sequence of the invention in a plant through the application of an exogenous chemical regulator. Depending upon the objective, the promoter may be a chemically inducible promoter, where application of the chemical induces gene expression, or a chemical-repressible promoter, where application of the chemical represses gene expression. Chemically inducible promoters are known in the art and include, but are not limited to, the maize In2-2 promoter, which is activated by benzenesulfonamide herbicide safeners, the maize GST promoter, which is activated by hydrophobic electrophilic compounds that are used as pre-emergent herbicides, and the tobacco PR-1a promoter, which is activated by salicylic acid. Other chemically regulated promoters of interest include steroid-responsive promoters (see, for example, the glucocorticoid-inducible promoter in Schena et al. (1991) *Proc. Natl. Acad. Sci. USA* 88:10421-10425 and McNellis et al. (1998) *Plant J.* 14(2):247-257) and tetracycline-inducible and tetracycline-repressible promoters (see, for example, Gatz et al. (1991) *Mol. Gen. Genet.* 227:229-237, and U.S. Pat. Nos. 5,814,618 and 5,789,156), herein incorporated by reference.

Where enhanced expression in particular tissues is desired, tissue-specific promoters can be utilized.

Tissue-specific promoters include those described by Yamamoto et al. (1997) *Plant J.* 12(2)255-265; Kawamata et al. (1997) *Plant Cell Physiol.* 38(7):792-803; Hansen et al. (1997) *Mol. Gen Genet.* 254(3):337-343; Russell et al. (1997) *Transgenic Res.* 6(2):157-168; Rinehart et al. (1996) *Plant Physiol.* 112(3):1331-1341; Van Camp et al. (1996) *Plant Physiol.* 112(2):525-535; Canevascini et al. (1996) *Plant Physiol.* 112(2):513-524; Yamamoto et al. (1994) *Plant Cell Physiol.* 35(5):773-778; Lam (1994) *Results Probl. Cell Differ.* 20:181-196; Orozco et al. (1993) *Plant Mol Biol.* 23(6):1129-1138; Matsuoka et al. (1993) *Proc Natl. Acad. Sci. USA* 90(20):9586-9590; and Guevara-Garcia et al. (1993) *Plant J.* 4(3):495-505.

So-called constitutive promoters may also be used in the methods of the present invention. Constitutive promoters include, for example, ubiq3At promoter, CaMV 35S promoter (Odell et al. (1985) *Nature* 313:810-812); rice actin (McElroy et al. (1990) *Plant Cell* 2:163-171); ubiquitin (Christensen et al. (1989) *Plant Mol. Biol.* 12:619-632 and Christensen et al. (1992) *Plant Mol. Biol.* 18:675-689); pEMU (Last et al. (1991) *Theor. Appl. Genet.* 81:581-588); MAS (Velten et al. (1984) *EMBO J.* 3:2723-2730); ALS promoter (U.S. application Ser. No. 08/409,297), and the like. Other constitutive promoters include those in U.S. Pat. Nos. 5,608,149; 5,608,144; 5,604,121; 5,569,597; 5,466,785; 5,399,680; 5,268,463; and 5,608,142.

A 'donor nucleic acid sequence' is one that comprises a sequence of interest that is capable of replacing a recipient chromosomal target site. Suitable sequences of interest include those that comprise repair polynucleotide repair sequences, that is to say sequences that will either introduce gain or loss of function into a targeted sequence which provides for a desired benefit in terms of genotype for a specific end purpose. For example, gain of function sequences may include introduction of point mutations, for example into the acetolactate synthase (ALS) gene of *Arabidopsis* which results in resistance of modified plants to sulfonylurea herbicide (Li et al., (1992) Plant Physiol, 100: 662-668). Other gene manipulations of gene expression that may be performed using methods of the invention include enhancement of gene expression in planta, for example by i) adding an enhancer of expression to the promoter region of a desired gene; ii) adding domains responsible for tissue specific expression. Other uses of methods of the invention include in planta addition of epitope tag domains for antibody detection to the nucleic acid sequence(s) (e.g. gene(s)) of interest, or fusion of specific nucleic acid sequence of interest, such as genes, to visual markers such as GFP and luciferase and the like. Loss of function sequences may include introduction of point mutations or deletions into specific genes, for example, the genes responsible for pod shattering in *Brassica* (cell wall hydrolases such as polygalacturonases, the regulatory regions of the corresponding plant genes (WO 1997/013865 and WO 1997/000417). The donor nucleic acid sequence may also comprise sequences that encode for the production of one or more proteins of interest in a plant. Suitable sequences include those that encode heterologous or exogenous proteins of interest for protein production purposes, or heterologous or exogenous sequences of interest that are used to introduce novel genetic pathways into plants that do not possess such pathways, such as nitrogen fixing pathway genes and/or cDNA sequences, genes for drought resistance, insect resistance and the like. Suitably, targeted protein production may be enhanced by employing methods of the invention on plant proteins and pharmaceutical proteins for use in mammals, including man, such as insulin, preproinsulin, proinsulin, glucagon, interferons such as α-interferon, β-interferon, γ-interferon, blood-clotting factors selected from Factor VII, VIII, IX, X, XI, and XII, fertility hormones including luteinising hormone, follicle stimulating hormone growth factors including epidermal growth factor, platelet-derived growth factor, granulocyte colony stimulating factor and the like, prolactin, oxytocin, thyroid stimulating hormone, adrenocorticotropic hormone, calcitonin, parathyroid hormone, somatostatin, erythropoietin (EPO), enzymes such as β-glucocerebrosidase, haemoglobin, serum albumin, collagen, insect toxic protein from *Bacillus thuringiensis*; herbicide resistance protein (glyphosate); salt-tolerance proteins; nutritional enhancement proteins involved in the biosynthesis of phenolics, starches, sugars, alkaloids, vitamins, and edible vaccines, and the like. Furthermore, the method of the invention can be used for the production of specific monoclonal antibodies or active fragments thereof and of industrial enzymes.

All proteins mentioned hereinabove are of the plant and human type. Other proteins that are contemplated for production in the present invention include proteins for use in veterinary care and may correspond to animal homologues of human proteins, such as the human proteins mentioned hereinabove.

The two flanking sequences may be selected from sub-terminal sequences that are capable of associating with donor binding domain of the MDRP and chromosomal DNA sequences under the mediation of specific DNA binding domains, such as tnpA as mentioned herein. Suitable sub-terminal sequences include sub-terminal regions of the CACTA super-family of transposable elements comprising repetitive motifs with affinity to tnpA-like protein domain(s) and the like.

The method described above, typically further comprises introducing a nucleic acid sequence that comprises a plant nuclear promoter operably linked to a third nucleic acid sequence that encodes for a viral replicase protein. Such viral replicase proteins include the Rep proteins of Geminiviruses (Gutierrez (1999) CMLS Cell Mol Life Sci., 56: 313-329) and these should be capable of binding to each of the said viral origins of replication provided on each end of the two flanking sequences of the donor DNA domain.

In an alternative, the method of the invention provides for the said second nucleic acid sequence comprising a primer binding site (PBS) that is fused to the 3' end of a right flanking border sequence as described herein. In this alternative aspect of the invention, a further nucleic acid sequence that comprises a plant nuclear promoter operably linked to a third nucleic acid sequence that encodes for a reverse transcriptase protein, such as RT-RH-tnt1, or a DNA encoding retrotransposon RNA or DNA encoding retroviral RNA, can be utilised. Suitable nucleic acid sequences include reverse transcriptase DNA sequence from Cauliflower mosaic virus (CaMV), yeast Ty1, plant Ty1-copia, Ty3-gypsy retrotransposon (Kumar & Bennetzen, (1999) Annual Review of Genetics, 33: 479-532) and other LTR retrotransposons. The primer binding site can be selected from a retrotransposon-specific primer binding site, and a primer binding site of a retrovirus. Preferably, the PBS is a retro-transposon-specific primer binding site.

The said third nucleic acid sequence may also be selected from the reverse transcriptase nucleic acid sequences from plant Ty1-copia, Ty3-gypsy retrotransposon (Kumar & Bennetzen, (1999) Annual Review of Genetics, 33: 479-532) and other LTR retrotransposons, for example, reverse transcriptase-RNase H.

Also provided are plant cells obtained according to a method of the invention as provided herein. Plant cells of the invention comprise a multi domain recombination protein that comprises:
i) a donor DNA-Binding Domain; and
ii) a chromosomal binding domain.

Preferably, a plant cell of the invention comprises a multi domain recombination protein that further comprises a third domain that is a chromosomal target binding domain. Preferably still, plant cells of the invention comprise a MDRP that comprises a fourth domain that is a recombination inducing domain.

A plant cell of the invention may be one selected from tobacco (*Nicotiana tabacum*) and other *Nicotiana species, arabidopsis*, potato, corn (maize), canola (rape), rice, wheat, barley, *brassica* sp. such as cauliflower, broccoli (e.g. green and purple sprouting), cabbage (e.g. red, green and white cabbages), curly kale, Brussels sprouts, cotton, algae (e.g. blue green species), lemnospora, or moss (e.g. *physcomitrella patens*), tomato, capsicum, squashes, sunflower, soyabean, carrot, melons, grape vines, lettuce, strawberry, sugar beet, peas, and sorghum. Especially preferred are plant cells of the invention that are selected from cotton, rice, oilseed *Brassica* species such as canola, corn (maize) and soyabean.

In a further aspect of the invention, there is provided a method of producing at least a heterologous or exogenous RNA species in a plant that comprises:
1) introducing into a regenerable plant cell a nucleic acid sequence that comprises a plant nuclear promoter operably linked to a first nucleic acid sequence that comprises a polynucleotide sequence encoding for an MDRP of the invention;
2) introducing into the said regenerable plant cell a second nucleic acid sequence that comprises
i) a donor nucleic acid sequence; and
ii) at least two flanking sequences that are located adjacent to each end of the donor polynucleotide sequence forming left and right borders thereto; and
iii) a viral origin of replication located 5' and 3' to each of the said left and right borders wherein said second nucleic acid sequence is operably linked to a plant nuclear promoter; and
3) introducing into the said regenerable plant cell a third nucleic acid sequence that encodes for a viral replicase protein wherein the third nucleic acid sequence is operably linked to a plant nuclear promoter or a native viral promoter;
4) growing said regenerable plant cell of steps 1) to 3);
5) selecting a plant cell of 4);
6) regenerating a plant from the plant cell of 5); and
7) growing the plant of 6.

Naturally, the man skilled in the art will appreciate that the flanking regions and the replicase protein will be capable of binding to a donor binding domain of the said multi domain recombination protein, and to the viral origin of replication sequences, respectively.

In a further aspect of the invention, there is provided a method of producing at least a heterologous or exogenous RNA species in a plant that comprises:
1) introducing into a regenerable plant cell a nucleic acid sequence that comprises a plant nuclear promoter operably linked to a first nucleic acid sequence that comprises a polynucleotide sequence encoding a MDRP of the invention;
2) introducing into the said regenerable plant cell a second nucleic acid sequence that comprises
i) a donor nucleic acid sequence;
ii) at least two flanking sequences that are located adjacent to each end of the donor polynucleotide sequence forming left and right borders thereto wherein said second nucleic acid sequence is operably linked to a plant nuclear promoter; and
iii) a primer binding site that is fused to the 3' end of the said right flanking border sequence;
3) introducing into the said regenerable plant cell a third nucleic acid sequence that encodes for a reverse transcriptase protein wherein the third nucleic acid sequence is operably linked to a plant nuclear promoter;
4) growing said regenerable plant cell of steps 1) to 3);
5) selecting a plant cell of 4);
6) regenerating a plant from the plant cell of 5); and
7) growing the plant of 6.

In a further aspect of the invention, there is provided an isolated polynucleotide sequence that comprises a donor nucleic acid sequence, at least two flanking sequences located adjacent to each end of the said donor polynucleotide sequences forming left and right borders thereto, and a viral origin of replication located 5' and 3' to each of the said left and right borders, respectively for use in a method of the invention. Furthermore, there is provided an isolated polynucleotide sequence according to this aspect of the invention that further comprises a third nucleic acid sequence that comprises a plant nuclear promoter or a native viral promoter operably linked to a first nucleic acid sequence that encodes for a viral replicase protein for use in a method according to the invention.

Nucleic acid vectors suitable for transformation of a plant or bacterial cell and including a polynucleotide encoding an MDRP of the invention are also provided. Such nucleic acid vectors are suitable for the transformation of a plant cell or of a prokaryote cell, such as an *Agrobacterium* cell.

Host cells containing a heterologous polynucleotide or nucleic acid vectors of the invention are also encompassed within the ambit of the invention, and include plant cells, and may be comprised in a plant, a plant part or a plant propagule, or an extract or derivative of a plant or in a plant cell culture. Thus, plants comprising plant cells of the invention are also encompassed within the ambit of the invention. Suitable plants of the invention include plants that are selected from the group consisting of tobacco (*Nicotiana tabacum*) and other *Nicotiana* species, such as *Nicotiana benthamiana*, carrot, vegetable and oilseed *Brassica*'s, melons, Capsicums, grape vines, lettuce, strawberry, sugar beet, wheat, barley, (corn) maize, rice, soybean, peas, sorghum, sunflower, tomato, cotton, and potato.

Preferred plants of the invention are those that are selected from the group consisting of cotton, rice, oilseed *Brassica* species such as canola, corn (maize) and soybean.

Naturally, the man skilled in the art will appreciate that terminator DNA sequences will be present in constructs used in the invention. A terminator is contemplated as a DNA sequence at the end of a transcriptional unit which signals termination of transcription. These elements are 3'-nontranslated sequences containing polyadenylation signals, which act to cause the addition of polyadenylate sequences to the 3' end of primary transcripts. For expression in plant cells the nopaline synthase transcriptional terminator (A. Depicker et al., 1982, J. of Mol. & Applied Gen. 1:561-573) sequence serves as a transcriptional termination signal.

Those skilled in the art are well able to construct vectors and design protocols for recombinant nucleic acid sequences or gene expression. Suitable vectors can be chosen or constructed, containing appropriate regulatory sequences, including promoter sequences, terminator fragments, polyadenylation sequences, enhancer sequences, marker genes and other sequences as appropriate. For further details see, for example, *Molecular Cloning: a Laboratory Manual:* 2nd edition, Sambrook et al, 1989, Cold Spring Harbor Laboratory Press. Many known techniques and protocols for manipulation of nucleic acid, for example in preparation of nucleic acid constructs, mutagenesis, sequencing, introduction of DNA into cells and gene expression, and analysis of proteins, are described in detail in *Current Protocols in Molecular Biology*, Second Edition, Ausubel et al. eds., John Wiley & Sons, 1992. The disclosures of Sambrook et al. and Ausubel et al. are incorporated herein by reference. Specific procedures and vectors previously used with wide success upon plants are described by Bevan (Nucl. Acids Res. 12, 8711-8721 (1984)) and Guerineau and Mullineaux (1993) (Plant transformation and expression vectors. In: Plant Molecular Biology Labfax (Croy RRD ed.) Oxford, BIOS Scientific Publishers, pp 121-148).

Naturally, the skilled addressee will appreciate that each introduced nucleic acid sequence will typically be under regulatory control of its own exogenous promoter and terminator. When two or more target proteins are destined to be produced from a single carrier RNA it is preferable if they are able to be readily separated, for example by binding to different protein-specific antibodies (monoclonal or polyclonal) in the harvesting phase of the plant cell culture system.

Selectable genetic markers may facilitate the selection of transgenic plants and these may consist of chimaeric genes that confer selectable phenotypes such as resistance to antibiotics such as spectinomycin, streptomycin, kanamycin, neomycin, hygromycin, puramycin, phosphinotricin, chlorsulfuron, methotrexate, gentamycin, spectinomycin, imidazolinones and glyphosate.

When introducing selected nucleic acid sequences according to the present invention into a cell, certain considerations must be taken into account, well known to those skilled in the art. The nucleic acid to be inserted should be assembled within a construct, which contains effective regulatory elements, which will drive transcription. There must be available a method of transporting the construct into the cell. Once the construct is within the cell membrane, integration into the endogenous chromosomal material either will or will not occur. Finally, as far as plants are concerned the target cell type must be such that cells can be regenerated into whole plants.

Plants transformed with DNA segments containing sequences of interest as provided herein may be produced by standard techniques, which are already known for the genetic manipulation of plants. DNA can be transformed into plant cells using any suitable technology, such as a disarmed Ti-plasmid vector carried by *Agrobacterium* exploiting its natural gene transfer ability (EP-A-270355, EP-A-0116718, NAR 12(22) 8711-87215 1984), particle or micro projectile bombardment (U.S. Pat. No. 5,100,792, EP-A-444882, EP-A-434616) microinjection (WO 92/09696, WO 94/00583, EP 331083, EP 175966, Green et al. (1987) *Plant Tissue and Cell Culture*, Academic Press), electroporation (EP 290395, WO 8706614) other forms of direct DNA uptake (DE 4005152, WO 9012096, U.S. Pat. No. 4,684,611), liposome mediated DNA uptake (e.g. Freeman et al. *Plant Cell Physiol.* 29: 1353 (1984)), or the vortexing method (e.g. Kindle, *PNAS U.S.A.* 87: 1228 (1990d) Physical methods for the transformation of plant cells are reviewed in Oard, 1991, *Biotech. Adv.* 9: 1-11.

Thus once a nucleic acid sequence or gene has been identified, it may be reintroduced into plant cells using techniques well known to those skilled in the art to produce transgenic plants of the appropriate phenotype.

*Agrobacterium* transformation is widely used by those skilled in the art to transform dicotyledonous species. Production of stable, fertile transgenic plants in almost all economically relevant monocot plants is also now routine: (Toriyama, et al. (1988) *Bio/Technology* 6, 1072-1074; Zhang, et al. (1988) *Plant Cell Rep.* 7, 379-384; Zhang, et al. (1988) *Theor. Appl. Genet* 76, 835-840; Shimamoto, et al. (1989) *Nature* 338, 274-276; Datta, et al. (1990) *Bio/Technology* 8, 736-740; Christou, et al. (1991) *Bio/Technology* 9, 957-962; Peng, et al. (1991) International Rice Research Institute, Manila, Philippines 563-574; Cao, et al. (1992) *Plant Cell Rep.* 11, 585-591; Li, et al. (1993) *Plant Cell Rep.* 12, 250-255; Rathore, et al. (1993) *Plant Molecular Biology* 21, 871-884; Fromm, et al. (1990) *Bio/Technology* 8, 833-839; Gordon-Kamm, et al. (1990) *Plant Cell* 2, 603-618; D'Halluin, et al. (1992) *Plant Cell* 4, 1495-1505; Walters, et al. (1992) *Plant Molecular Biology* 18, 189-200; Koziel, et al. (1993) *Biotechnology* 11, 194-200; Vasil, I. K. (1994) *Plant Molecular Biology* 25, 925-937; Weeks, et al. (1993) *Plant Physiology* 102, 1077-1084; Somers, et al. (1992) *Bio/Technology* 10, 1589-1594; WO92/14828). In particular, *Agrobacterium* mediated transformation is now a highly efficient alternative transformation method in monocots (Hiei et al. (1994) *The Plant Journal* 6, 271-282).

The generation of fertile transgenic plants has been achieved in the cereals rice, maize, wheat, oat, and barley (reviewed in Shimamoto, K. (1994) *Current Opinion in Biotechnology* 5, 158-162.; Vasil, et al. (1992) *Bio/Technology* 10, 667-674; Vain et al., 1995, *Biotechnology Advances* 13 (4): 653-671; Vasil, 1996, *Nature Biotechnology* 14 page 702). Wan and Lemaux (1994) *Plant Physiol.* 104: 37-48 describe techniques for generation of large numbers of independently transformed fertile barley plants.

Micro projectile bombardment, electroporation and direct DNA uptake are preferred where *Agrobacterium* is inefficient or ineffective. Alternatively, a combination of different techniques may be employed to enhance the efficiency of the transformation process, e.g. bombardment with *Agrobacterium* coated micro particles (EP-A-486234) or micro projectile bombardment to induce wounding followed by co-cultivation with *Agrobacterium* (EP-A-486233).

Following transformation, a plant may be regenerated, e.g. from single cells, callus tissue or leaf discs, as is standard in the art. Almost any plant can be entirely regenerated from cells, tissues and organs of the plant. Available techniques are reviewed in Vasil et al., *Cell Culture and Somatic Cell Genetics of Plants, Vol. I, II and III, Laboratory Procedures and Their Applications*, Academic Press, 1984, and Weiss Bach and Weiss Bach, *Methods for Plant Molecular Biology*, Academic Press, 1989.

The particular choice of a transformation technology will be determined by its efficiency to transform certain plant species as well as the experience and preference of the person practising the invention with a particular methodology of choice. It will be apparent to the skilled person that the particular choice of a transformation system to introduce nucleic acid into plant cells is not essential to or a limitation of the invention, nor is the choice of technique for plant regeneration.

The invention further encompasses a host cell transformed with vectors or constructs as set forth above, especially a plant or a microbial cell. Thus, a host cell, such as a plant cell, including nucleotide sequences of the invention as herein indicated is provided. Within the cell, the nucleotide sequence may be incorporated within the chromosome.

Also according to the invention there is provided a plant cell having incorporated into its genome at least a nucleotide sequence, particularly heterologous nucleotide sequences, as provided by the present invention under operative control of regulatory sequences for control of expression as herein described. The coding sequence may be operably linked to one or more regulatory sequences which may be heterologous or foreign to the nucleic acid sequences employed in the invention, such as those not naturally associated with the nucleic acid sequence(s) for its (their) expression. The nucleotide sequence according to the invention may be placed under the control of an externally inducible promoter to place expression under the control of the user. A further aspect of the present invention provides a method of making such a plant cell involving introduction of nucleic acid sequence(s) contemplated for use in the invention or a suitable vector including the sequence(s) contemplated for use in the invention into a plant cell and causing or allowing recombination between the vector and the plant cell genome to introduce the said sequences into the genome. The invention extends to plant cells containing a nucleotide sequence according to the invention as a result of introduction of the nucleotide sequence into an ancestor cell.

The term "heterologous" may be used to indicate that the gene/sequence of nucleotides in question have been introduced into said cells of the plant or an ancestor thereof, using genetic engineering, ie by human intervention. A transgenic plant cell, i.e. transgenic for the nucleotide sequence in question, may be provided. The transgene may be on an extra-genomic vector or incorporated, preferably stably, into the genome. A heterologous gene may replace an endogenous equivalent gene, ie one that normally performs the same or a similar function, or the inserted sequence may be additional to the endogenous gene or other sequence. An advantage of introduction of a heterologous gene is the ability to place expression of a sequence under the control of a promoter of choice, in order to be able to influence expression according to preference. Furthermore, mutants, variants and derivatives of the wild-type gene, e.g. with higher activity than wild type, may be used in place of the endogenous gene. Nucleotide sequences heterologous, or exogenous or foreign, to a plant cell may be non-naturally occurring in cells of that type, variety or species. Thus, a nucleotide sequence may include a coding sequence of or derived from a particular type of plant cell or species or variety of plant, placed within the context of a plant cell of a different type or species or variety of plant. A further possibility is for a nucleotide sequence to be placed within a cell in which it or a homologue is found naturally, but wherein the nucleotide sequence is linked and/or adjacent to nucleic acid which does not occur naturally within the cell, or cells of that type or species or variety of plant, such as operably linked to one or more regulatory sequences, such as a promoter sequence, for control of expression. A sequence within a plant or other host cell may be identifiably heterologous, exogenous or foreign.

Plants which include a plant cell according to the invention are also provided, along with any part or propagule thereof, seed, selfed or hybrid progeny and descendants. Particularly provided are transgenic crop plants, which have been engineered to carry genes identified as stated above. Examples of suitable plants include tobacco (*Nicotiana tabacum*) and other *Nicotiana* species, carrot, vegetable and oilseed *Brassica*'s, melons, Capsicums, grape vines, lettuce, strawberry, sugar beet, wheat, barley, (corn) maize, rice, soyabean, peas, sorghum, sunflower, tomato, cotton, and potato. Especially preferred transgenic plants of the invention include cotton, rice, oilseed *Brassica* species such as canola, corn (maize) and soyabean.

In addition to a plant, the present invention provides any clone of such a plant, seed, selfed or hybrid progeny and descendants, and any part of any of these, such as cuttings, seed. The invention provides any plant propagule that is any part which may be used in reproduction or propagation, sexual or asexual, including cuttings, seed and so on. Also encompassed by the invention is a plant which is a sexually or asexually propagated off-spring, clone or descendant of such a plant, or any part or propagule of said plant, offspring, clone or descendant.

The present invention also encompasses the polypeptide expression product of a nucleic acid molecule according to the invention as disclosed herein or obtainable in accordance with the information and suggestions herein. Also provided are methods of making such an expression product by expression from a nucleotide sequence encoding therefore under suitable conditions in suitable host cells e.g. *E. coli*. Those skilled in the art are well able to construct vectors and design protocols and systems for expression and recovery of products of recombinant gene expression.

"Homology" in relation to an amino acid sequence or polypeptide sequence produced by the method of the invention may be used to refer to identity or similarity, preferably identity. As noted already above, high level of amino acid identity may be limited to functionally significant domains or regions.

In certain embodiments, an allele, variant, derivative, mutant derivative, mutant or homologue of the specific sequence may show little overall homology, say about 20%, or about 25%, or about 30%, or about 35%, or about 40% or about 45%, with the specific sequence. However, in functionally significant domains or regions, the amino acid homology may be much higher. Putative functionally significant domains or regions can be identified using processes of bioinformatics, including comparison of the sequences of homologues.

Functionally significant domains or regions of different polypeptides may be combined for expression from encoding nucleic acid as a fusion protein. For example, particularly advantageous or desirable properties of different homologues may be combined in a hybrid protein, such that the resultant expression product, may include fragments of various parent proteins, if appropriate.

Similarity of amino acid sequences may be as defined and determined by the TBLASTN program, of Altschul et al. (1990) *J. Mol. Biol.* 215: 403-10, which is in standard use in the art. In particular, TBLASTN 2.0 may be used with Matrix BLOSUM62 and GAP penalties: existence: 11, extension: 1. Another standard program that may be used is BestFit, which is part of the Wisconsin Package, Version 8, September 1994, (Genetics Computer Group, 575 Science Drive, Madison, Wis., USA, Wisconsin 53711). BestFit makes an optimal alignment of the best segment of similarity between two sequences. Optimal alignments are found by inserting gaps to maximize the number of matches using the local homology algorithm of Smith and Waterman (*Adv. Appl. Math.* (1981) 2: 482-489). Other algorithms include GAP, which uses the Needleman and Wunsch algorithm to align two complete sequences that maximizes the number of matches and minimizes the number of gaps. As with any algorithm, generally the default parameters are used, which for GAP are a gap creation penalty=12 and gap extension penalty=4. Alternatively, a gap creation penalty of 3 and gap extension penalty of 0.1 may be used. The algorithm FASTA (which uses the method of Pearson and Lipman (1988) *PNAS USA* 85: 2444-2448) is a further alternative.

Use of either of the terms "homology" and "homologous" herein does not imply any necessary evolutionary relationship between compared sequences, in keeping for example with standard use of terms such as "homologous recombination" which merely requires that two nucleotide sequences are sufficiently similar to recombine under the appropriate conditions. Further discussion of polypeptides according to the present invention, which may be encoded by nucleic acid according to the present invention, is found below.

The teaching of all references cited herein is incorporated in its entirety into the present description.

There now follow non-limiting examples and figures illustrating the invention.

FIGURES

FIG. 1: Structure of multi-domain recombination protein used for gene targeting in plant cells. CBD=chromosomal binding domain; TBD=target binding domain; DBD=donor binding domain; RID=recombination inducing domain.

Figure 2:
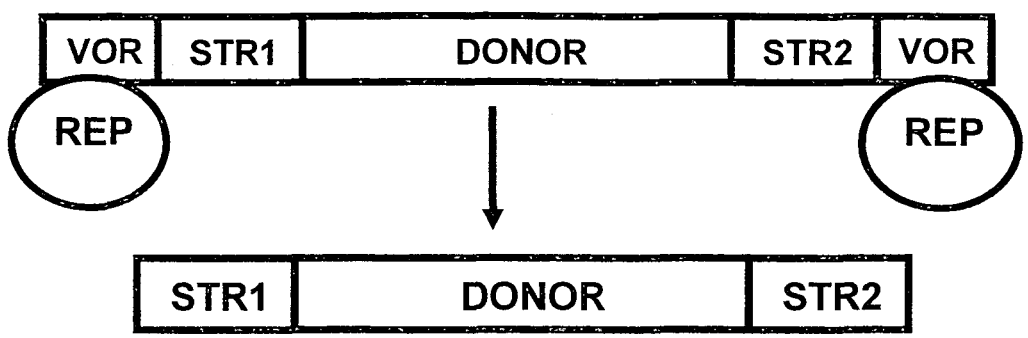
Figure 2:
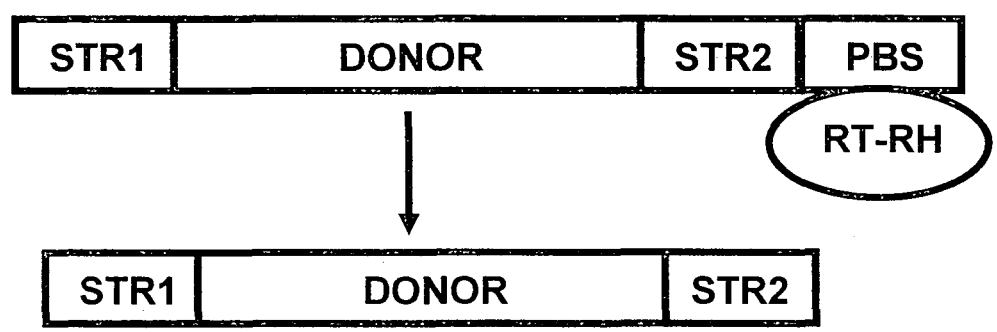

FIG. 2: Vector systems suitable for the amplification of donor DNA fragments in plant cells.

(A) Viral system for DNA amplification: VOR—viral origin of replication; STR1, STR2—sub-terminal regions with affinity to donor binding domain of multi-domain recombination protein; DONOR—donor fragment of DNA for gene targeting; REP—viral replicase protein which binds to VOR and induces replication of donor DNA.

(B) Retrotransposon RNA-based system of DNA amplification. Donor fragment is fused to a primer binding site (PBS) and is expressed from a strong plant specific promoter. The generated RNA is subsequently used for a reverse transcription reaction using retrotransposon specific reverse transcriptase. PBS—primer binding site used for primer annealing (tRNA-Met used as a primer) and reverse transcription of donor RNA into DNA; RT—RH—retrotransposon specific Reverse Transcriptase-RNase H protein which binds to PBS and initiates reverse transcription.

Figure 3:
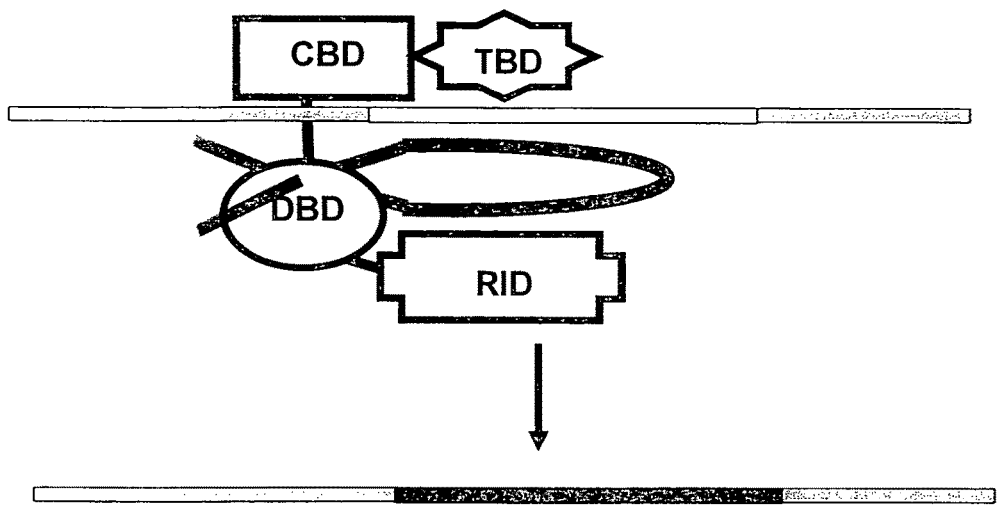

FIG. 3: Schematic presentation of gene targeting using multi-domain recombination protein.

Figure 4:
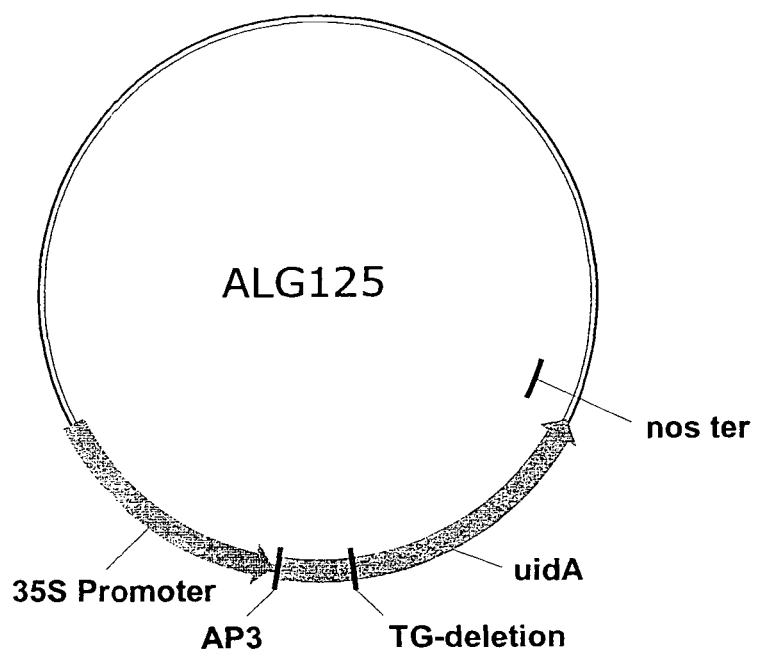

FIG. 4: Deleterious construct ALG125 used for *Arabidopsis* transformation.

Figure 5:
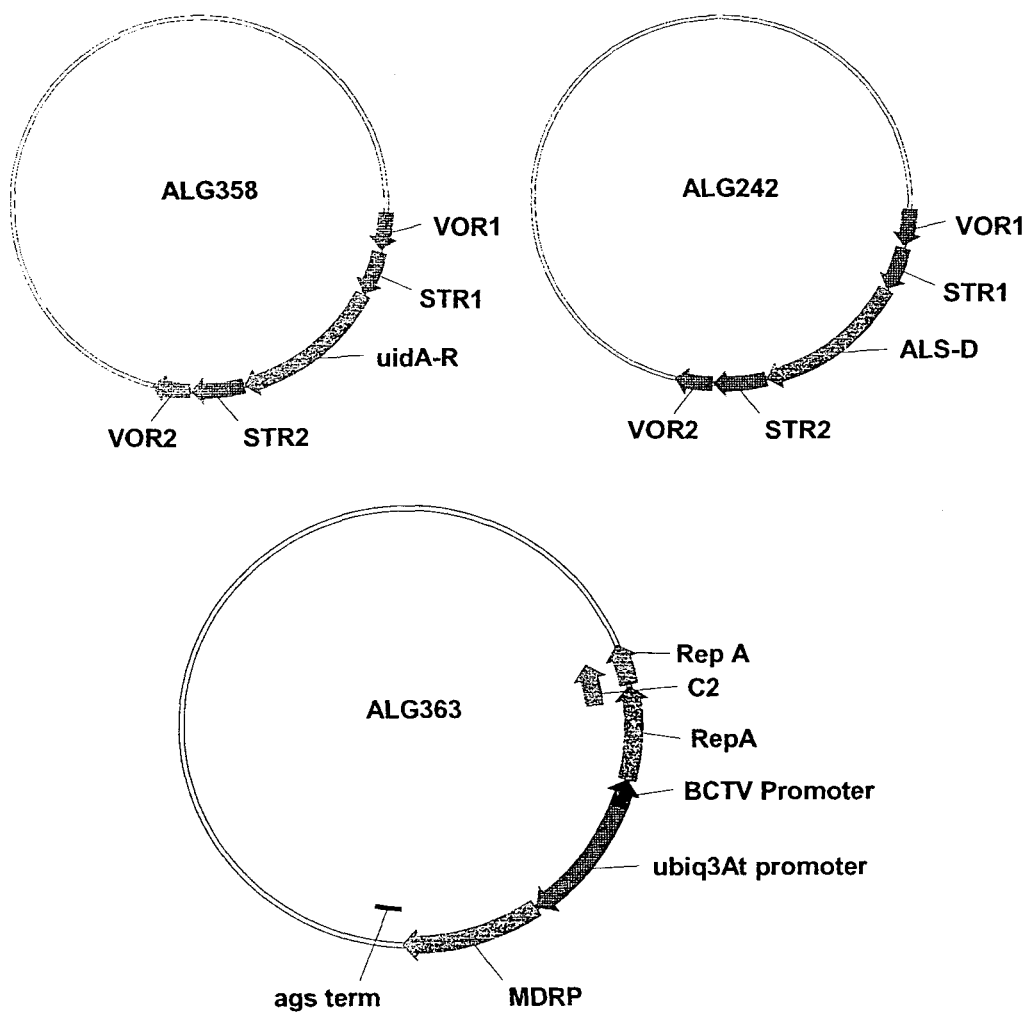

FIG. 5: A set of constructs for gene targeting using viral donor amplification system.

Figure 6:
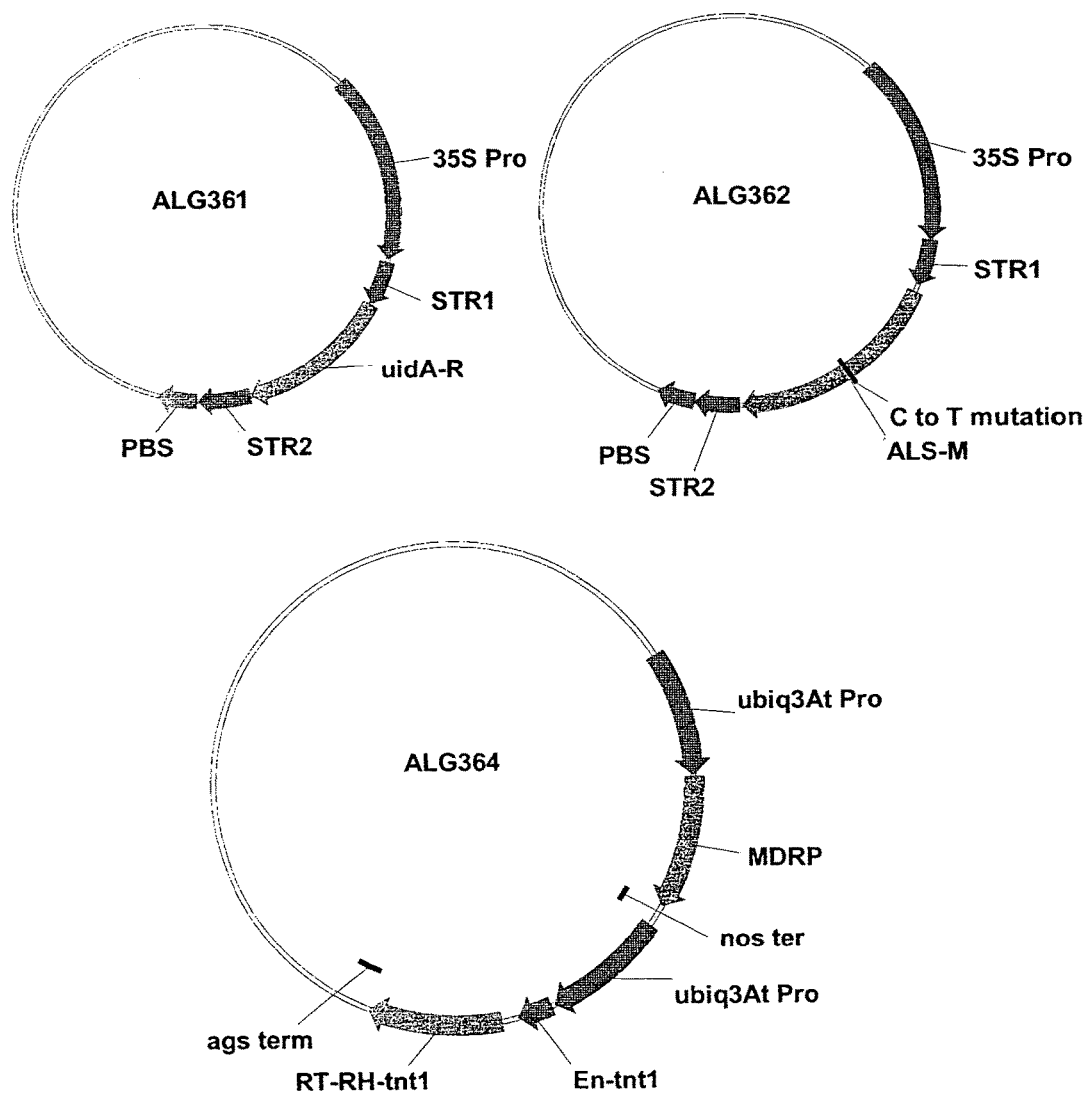

FIG. 6: Set of constructs for gene targeting using the retrotransposon RNA-based donor amplification system.

Figure 7:
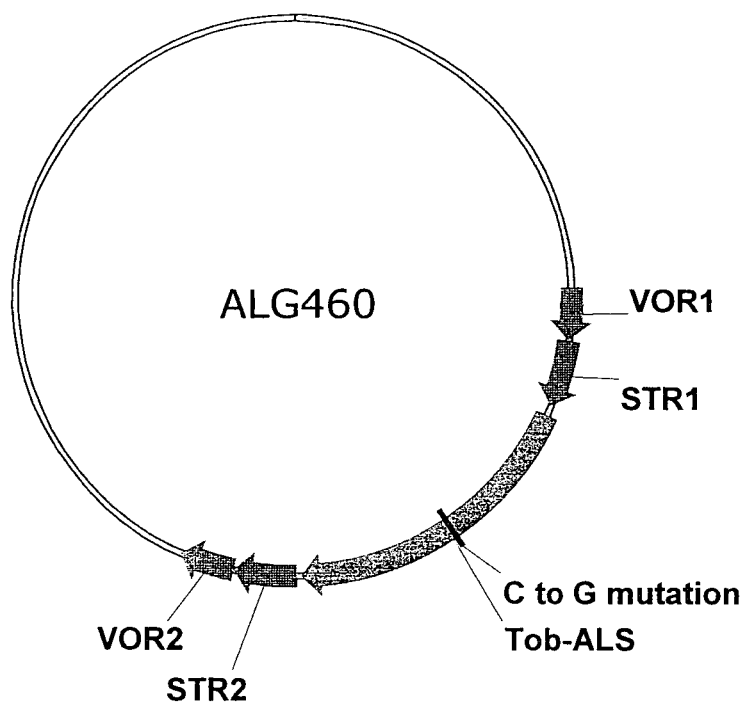

FIG. 7: ALG460 construct for mutagenesis of tobacco acetolactate synthase gene (ALS).

Figure 8:
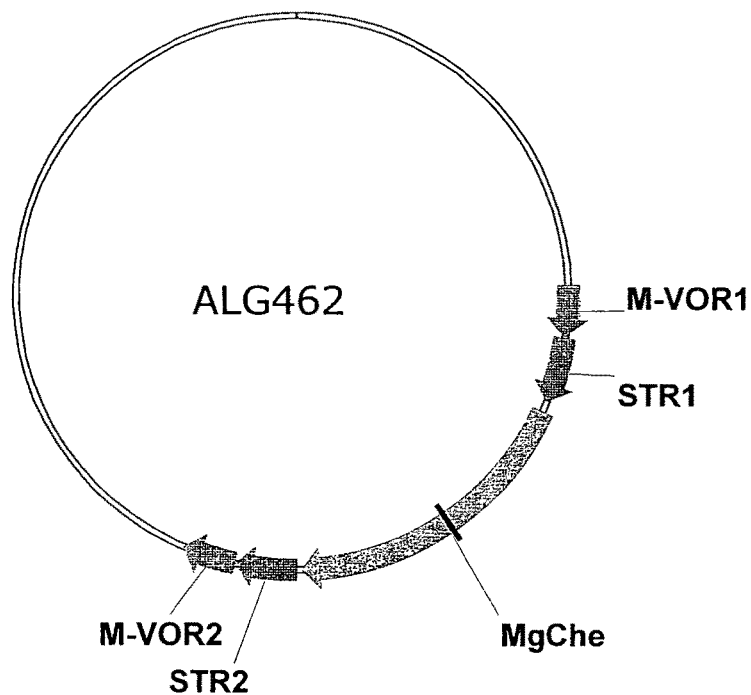
Figure 8:
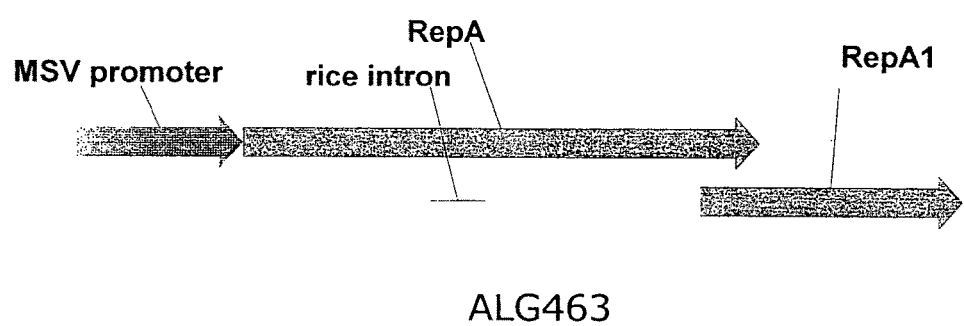

FIG. 8: A set of constructs for targeting of magnesium chelatase in rice.

EXPERIMENTAL SECTION

Concept

We have developed a robust and reproducible technique for site-specific modification at sites within the plant nuclear genome. The essence of gene targeting as developed herein lies in the efficient placing of donor DNA alongside the DNA of a targeting site and the induction of recombination between these two DNA fragments. Our gene targeting technique is based on two essential components:

(1) a multi-domain recombination protein (MDRP); and
(2) donor amplification vector (DAV).

The MDRP has the following functionalities:
(i) able to bind to donor DNA;
(ii) able to bind to chromosomal DNA;
(iii) able to search and locate target DNA; and
(iv) able to initiate the annealing of homologous DNA strands between target and donor DNA.

The DAV is a tool for the amplification of a donor fragment or donor fragments of DNA of interest in a plant cell, providing a permanent and abundant supply of donor DNA molecules for efficient gene targeting.

Multi-domain Recombination Protein (MDRP)

The Multi-domain recombination protein is at the core of our gene targeting technology and it functions as an efficient device for the induction of recombination between target and donor DNA molecules. It comprises four major domains (1) a donor DNA-binding domain; (2) a chromosomal DNA binding domain; (3) a target binding domain; and (4) a recombination inducing domain (see FIG. 1).

The Donor DNA-Binding Domain (DBD) is required for efficient capturing of donor DNA molecules and the formation of a donor DNA-protein complex (DPC).

The Chromosomal Binding Domain (CBD) is required for the binding of the DPC to the chromosomal DNA of interest, and serves as an engine for driving the donor DPC along the chromosomal DNA facilitating an active search for a target site.

The Target Binding Domain (TBD) facilitates recognition of a target site on the chromosome and increases the efficiency of alignment of a donor DNA fragments and target DNA fragments.

The Recombination Inducing Domain (RID) is required for the first step of homologous recombination: the annealing of a donor DNA with the DNA of a targeting site.

Vector Systems Suitable for Donor Amplification

To provide an excess of donor DNA molecules for gene targeting, donor amplification vectors were designed. We have developed two systems for donor amplification:

(1) a viral DNA amplification system; and
(2) a retrotransposon RNA-based system of DNA amplification (see FIG. 2).

(1) Viral DNA amplification system is based on the placing of a viral origin of replication (VOR) from a DNA virus (for example from plant geminiviruses such as beet curly top virus (BCTV), tobacco golden mosaic virus (TGMV), maize streak virus (MSV) etc.) on both flanks or ends of a donor DNA fragment that comprises the donor DNA fragment and sub-terminal DNA sequences with high affinity to donor binding domain of the MDRP fused to both ends thereof. Thus, the donor DNA fragment has attached at each flank or end, a sub-terminal DNA sequences and fused to each of these is a VOR as depicted in FIG. 2. Co-expression of a VOR specific replicase generates replication of the DNA fragment of interest that is placed or located between the two flanking viral origins of replication. As a result a great abundance or excess of single-stranded DNA (ssDNA) or double-stranded DNA (dsDNA) fragments of donor DNA are produced in the plant nucleus. The two additional sub-terminal DNA sequences are referred to as "STR1" and "STR2" in FIG. 2.

(2) Retrotransposon RNA-based system of DNA amplification is based on the generation of RNA from a transgene cassette containing a donor DNA fragment (flanked by an STR1 and STR2) fused to a retrotransposon-specific primer binding site (PBS). The PBS is capable of capturing cellular tRNA-Met, and uses it as a primer for a reverse transcription reaction. Co-expression of a retrotransposon specific Reverse Transcriptase or Reverse Transcriptase-RNase H(RT-RH) sequence, such as a cDNA or full length gene sequence, facilitates reverse transcription of the transcript from the donor cassette into single-stranded DNA which is then subsequently used as a DNA donor for gene targeting.

In summary, the donor amplification vector system generates a constantly abundant amount or excess of donor DNA. The donor binding domain (DBD) of the multi-domain recombination protein binds to STR1 and STR2 regions of donor DNA molecules. Chromosomal binding domains (CBD) and target binding domains (TBD) perform a search for a target DNA site and place a donor DNA molecule alongside the targeting site. The recombination inducing domain (RID) of the multi-domain recombination protein (MDRP) initiates annealing between donor DNA and target DNA with subsequent involvement of the host gene repair machinery which accomplishes the process of replacement of the target DNA fragment with the donor DNA (see FIG. 3).

Material and Methods
Design of Multi-domain Recombination Protein (MDRP)

In order to build a multi-domain recombination protein (MDRP) a partial sequence of tnpA protein (1-543 aa) from the maize En/Spm transposable element comprising a DNA binding domain (between position 122 to 427) was used as a core. This DNA domain has a strong affinity to 12 bp motifs in the sub-termini of the En/Spm transposon (Gierl et al., (1988) EMBO J, 7, 4045-4053) and represents a donor binding domain (DBD) of MDRP. Six hyper-reactive 12 bp motifs at the left sub-terminal region (STR1) and eight at the right sub-terminal region (STR2) of En/Spm DNA sequence were detected, and these sub-terminal regions are utilised as flanking regions for the donor fragment in the donor amplification vector. The tnpA protein also mediates association of STR1—STR2 DNA regions with chromosomal DNA sequences (Masson et al., (1991) Plant Cell, 3, 73-85), and as a result can fulfil the second function as a chromosomal DNA binding domain (CBD) of MDRP.

It has been shown that homologous DNA pairing—the key reaction of homologous recombination—can be promoted by a 20 amino acid peptide derived from the recA protein of *E. coli* (Voloshing et al., (1996) Nature, 272, 868-872). We have fused this short recA peptide with tnpA protein resulting in tnpAA protein, and utilised it as the recombination inducing domain (RID) of the MDRP. These three fused domains represent the backbone of our MDRP. Donor binding domain (DBD) and chromosomal binding domain (CBD) may also be selected from other mobile genetic elements such as TAM3, Ac-Dc, Mutator transposons (Hehl et al., (1991) Plant Mol Biol, 16, 369-371; Kunze et al., (1987) EMBO J, 6, 1555-1563, Brown et al., (1992) Genetics, 130, 889-898), Ty1-copia, Ty3-gypsy groups of retrotransposons (Kumar & Bennetzen (1999) Ann Review Genet, 33, 479-532), and DNA binding domains from bacterial restriction endonucleases, such as the well characterised EcoRV restrictase (Shulze et al., (1998) EMBO J, 17, 6757-6766; Kessler & Manta (1990) Gene, 92, 1-248).

The recombination inducing domain (RID) may be selected from well characterised proteins involved in induction of homologous recombination such as rad51, rad52 etc. (Symington, (2002) Microbiology and Molecular Biology Reviews, 66, 630-670).

The target binding domain (TBD) of the MDRP should be designed according to the sequence of the targeting site. The ideal target recognition domains may be represented by zinc-finger nucleases (ZFN) and meganuclease (MN) binding domains (Bibikova et al., (2003) Science, 300, 764-766; Epinat et al., (2003) Nuc Acid Res, 31, 2952-2962). The TBD may also be selected from gene specific DNA-binding proteins such as transcription factors, MADS domain proteins etc (Pellegrini et all., (1995) Nature, 376, 490-498; Schwechheimer et al., (1998) Ann Review Plant Physiol Plant Mol Biol., 49, 127-150). As an example we utilised a DNA-binding domain from *Arabidopsis* MADS domain protein, APETALA1, which recognises DNA sequence of the APETALA3 gene as a target recognition domain.

Design of Vector System for Donor Amplification

Typically, a DNA fragment of 500-2000 bp with homology to DNA of a desirable targeting site is used as a donor for gene targeting. In order to provide affinity of donor DNA molecules to the donor binding domain of the MDRP, the STR1 and STR2 sub-terminal sequences from the maize En/Spm transposon containing 12 bp repetitive motifs were fused to the designed donor fragment (FIG. 2). These sequences play an important role in recognition and recruitment of the donor DNA molecules by the MDRP.

Two different systems for amplification of donor DNA molecules in plant cells can be utilised. For the viral system of donor amplification, we utilised the viral origin of replication (VOR) from beet top curly virus (BCTV) (Stanley et al., (1986) EMBO J, 5, 1761-1767), which was placed at both ends of the donor DNA fragment (FIG. 2A). The viral DNA fragment containing promoter and replicase repA gene (REP) was co-delivered together with donor amplification vector to initiate replication of the donor fragment in the plant cells (FIG. 5). For monocots a maize streak virus origin of replication was used in a similar way to the BCTV origin of replication. The whole viral sequence may also be used as a source of replicase.

The retrotransposon RNA-based system of DNA amplification (FIG. 2B) is based on the generation of RNA from a transgene cassette containing donor fragment fused to a retrotransposon-specific primer binding site (PBS). We have utilised PBS from tobacco tnt1 retrotransposon (Casacuberta et al., (1993), Nuc Acids Res., 21, 2087-2093), which recruits cytoplasmic tRNA-Met as a primer for reverse transcription.

Partial sequences of tnt1 expressed polypeptide representing endonuclease (En) and reverse transcriptase (RT) domains (En-RT), or combination of En, RT and RNase H(RH) domains (En-RT-RH) was co-delivered under a plant specific promoter to generate reverse transcriptase enzyme (FIG. 6).

Transformation of *Arabidopsis* Plants

Transformation of *Arabidopsis* plants was performed as described in Clough & Bent (1998) Plant Journal 16:735-743). *Agrobacterium tumefaciens* strain GV3101 (Koncz & Schell (1986) Mol Gen Genet 204:383-396) was used for transformation.

Transformation of Tobacco Leaf Explants with *Agrobacterium* Strain AGL1

All items are autoclave-sterilised prior to use.

Filter sterilize antibiotics to prevent fungal growth, keep antibiotics for plant tissue culture in separate box.

Sterilize plant material: take plants of about 9 cm high which have not started to flower. Cut leaves having a cuticle (4-6 leaves per construct, enough to cut 100 explants), dip in 70% Ethanol and immediately dip in 1% Na-hypochlorite (cat. No 01032500; use bottle of bleach that is ≤3 months old because the chlorine gas evaporates), hold leaves with forceps and stir in it for 20 min. Avoid damaging the cuticle otherwise bleach will enter the vascular system. Rinse briefly in sterile water 5-6 times and leave in water until ready to be cut.

Co-cultivation of *agrobacterium* with tobacco explants: grow AGL1 in LB or L broth with appropriate antibiotics overnight at 28-30° C., the next day re-suspend agro in co-cultivation solution so that the final concentration is around 0.4-0.6 $OD_{600nm}$. Place tobacco leaves in co-culture broth and cut squares of 1-1.5 cm×1-1.5 cm with a rounded sterile scalpel using a rolling action. Dip the leaf explants in the agro solution with sterile forceps (stored in 100% ethanol, flamed and let to cool prior to touching the leaf tissue) blot on sterile Whatman paper and transfer on non-selective TSM plates (6 explants per plate) need to prepare about 15 plates per construct. Repeat this procedure for each construct, making sure that the scalpel and forceps are dipped in ethanol and flamed between each construct to prevent cross-contamination. Leave for 2 days only for AGL1 (3-4 days for other agro strains)

Transfer on selective TSM plates: use sterile flamed forceps to pick up and wash explants in 100 mls co-cultivation broth supplemented with timentin 320 mg/l (one pot per construct), shake well, blot on sterile whatman paper and place the washed explants on selective TSM plates supplemented with appropriate selective antibiotics and timentin 320 mg/l to kill agrobacterium.

Shoot regeneration: takes around 1 month to see shoots appear, explants should be transferred on fresh plates every 10-14 days. Watch out for AGL1 recurrent growth, if Timentin is not enough to kill *agrobacterium*, add cefotaxime at 250 mg/l.

Root regeneration: Takes around 1 week. Shoots are cut from the explants and place in growth boxes containing TRM supplemented with the appropriate selective antibiotics and timentin 320 mg/l cefotaxime 250 mg/l to prevent *agrobacterium* recurrent growth.

Maintain plants in TRM boxes: sub them every two weeks until ready to be transferred into glasshouse Adaptation to glasshouse conditions: soak peat pellets in sterile water until they swell to normal size and carefully plant one plant per pellet, incubate the plants under 100% humidity conditions in a propagator, gradually opening the little windows until plants adapt to normal atmosphere over several days.

Recipes:

Co-culture: MS with vitamins and MES+0.1 mg/l NAA+1 mg/l BA +3% sucrose, pH 5.7

TSM: MS with vitamins and MES+0.1 mg/l NAA+1 mg/l BA+3% sucrose, pH5.7, 0.2% gelrite TRM: MS salts with vitamins and MES+0.5% sucrose, pH5.7, 0.2% gelrite.

Autoclave.

Antibiotics Concentration

For *agrobacterium* LB or L Cultures:

To grow AGL1 carrying pGreen/pSOUP: Carbenicillin 100 mg/l, Tetracycline 5 mg/ml, Rifampicin 50 mg/ml, Kanamycin 50 mg/ml AGL1 carrying pSOUP: Carbenicilin 100 mg/l, Tetracycline 5 mg/ml, Rifampicin 50 mg/ml.

AGL1 empty: Carbenicillin 100 mg/l, Rifampicin 50 mg/ml.

For Plant Culture:

Kanamycin: 300 mg/l (100 mg/l if using benthamiana)

Hygromycin: 30 mg/l (10 mg/l if using benthamiana)

PPT: 20 mg/l (2 mg/l if using benthamiana)

Timentin: 320 mg/l. It is used to kill *agrobacterium*, fairly unstable make up small amount of stock, store in freezer for up to 1 month after that the antibiotic is no more efficient.

Cefotaxime: 250 mg/l. Also used to kill *agrobacterium*, add to TS.

Transformation of Rice Immature Embryos.

Immature Embryo Excision

Day 1:

Remove milky/post-milky stage immature seeds from panicles (immature embryos 1-2 mm in size are desired).

Sterilize immature seeds: 50% sodium hypochlorite (12%)+1 drop of tween 20. Shake 10 min.

Rinse 3-5× in sterile deionised water. Drain off surplus water. Aliquot seeds (around 40) in sterile Petri dishes.

Set up a 60×15 mm Petri dish containing a 50% sodium hypochlorite solution and next to this a sterile beaker on its side with a sterile filter paper in it. Use sterile forceps to aseptically remove glumes from the first seed. Immerse this seed in the 50% sodium hypochlorite. Remove glumes from a second seed and immerse the second seed into the sodium hypochlorite solution whilst removing the first seed and storing this dehusked/sterilized seed on the filter paper in the beaker. Continue.

After all the glumes are removed:

Sterilize dehusked seeds: 50% sodium hypochlorite: 5 min. with agitation.

Rinse: 5-7× in sterile deionized water, drain.

Place all seeds in a large sterile Petri dish. Aliquot for embryo excision (to keep seeds from drying out, work with only 50-100 in the plate at a time leaving the rest in the master plate).

Remove the embryo from each seed and place embryo, scutellum up, in a 90×15 mm Petri dish containing proliferation medium (40-50 embryos/plate). Culture at 28∈ C in the dark for 2 days prior to bombardment Day 3:

Check Each Embryo for contamination before blasting

Remove the embryos from the proliferation medium. Distribute 35-40 embryos scutellum upwards in an area 1 $cm^2$ in the centre of a 60×15 mm target plate containing 10 ml of proliferation medium+osmoticum (0.6M). Check each target plate so that the scutellum is straight. Allow enough room so the scutella do not shade each other out.

Bombardment:

| Biolistic Gun | 14 kV (PDS-1000/He Instrument (BioRad) Vacuum: 25 inches of Hg |
|---|---|
| 1st bombardment | 4 hours after osmoticum treatment |
| 2nd bombardment | 4 hours after 1st bombardment |

Day 4:

4-16 hours after the 2nd blast transfer immature embryos to proliferation medium without osmoticum. Culture in the dark at 28° C. for 2 days.

Selection:

Day 5:

Aseptically cut out with scissors the germinating shoot. Transfer 16-20 immature embryos to fresh proliferation medium containing 30-50 mg/l Hygromycin (depending on the genotype); culture in the dark at 28° C.; record total number of embryos.

After 10 days carefully remove the callus from the scutellum by breaking it up into 2-10 small pieces; subculture onto fresh proliferation medium+hygromycin. Do not subculture brown tissue and remaining immature embryo which could inhibit further growth of healthy callus.

Subculture every 10 days by selecting healthy tissue: (embryogenic if present) and transfer it to fresh proliferation medium+hygromycin. Remove brown callus as it could be inhibiting to embryogenic callus.

30 to 40 days after bombardment change selection procedure. Instead of eliminating bad-looking tissue keep embryogenic tissue only (eliminate healthy non-embryogenic tissue)

Regeneration:

After 40 to 60 days, transfer established embryogenic callus showing differential growth on proliferation medium+ hygromycin to regeneration medium+hygromycin. Culture at 28∈ C under low light for 10 days then under high light for 10 additional days. Check plates periodically in the light for the development of embryos and green shoots. As shoots develop it is sometimes beneficial to gently move the developing shoot away from the callus it originated from and remove any dead tissue from the shoot itself to prevent inhibition of growth.

Germination:

Transfer white compact embryos and green shoots initiating roots to the germination medium under high light at 28∈ C for 1 to 2 weeks. Check plates periodically. Remove necrotic tissue and divide germinating embryos if necessary.

Results

To assess efficiency of gene targeting in *Arabidopsis* a set of constructs was prepared for targeting of exogenous and endogenous genes (FIGS. 5-6). An exogenous uidA gene from *E. coli* and *Arabidopsis* endogenous acetolactate synthase (ALS) gene were used for targeting.

Two base pair deletion was introduced in uidA gene from *E. coli* and mutated fragment was fused to AP3 domain. Modified uidA gene was introduced in *Arabidopsis* under CMV 35S promoter and nos terminator (construct ALG125, FIG. 4). The transgenic lines were assayed for GUS activities as described by McCabe et al., (Bio/Technol, 1988, 6, 923-926). No GUS activity was detected in transgenic lines due to frame shift in the uidA gene OFR. The *Arabidopsis* plants carrying deleterious uidA gene were then co-transformed with repair donor constructs ALG358 and ALG363 construct carrying source of replicase and MDRP (FIG. 5). Subsequent generation was assessed for GUS activities and large blue sectors were observed on leaves of about 40% of transgenic lines, confirming repair of the uidA gene in planta using our gene targeting system. Similar data was obtained with the retrotransposon RNA-based donor amplification vector. A point mutation was introduced into the donor fragment for *Arabidopsis* endogenous acetolactate synthase gene (ALS) and constructs ALG242 and ALG362 were prepared for ALS targeting (FIGS. 5-6). It has been demonstrated that replacement of the C-residue by T-residue in position 589 of the gene confers chlorsulfuron herbicide resistance in *Arabidopsis* plants (Haughn & Somerville, (1986) Mol Gen Genet, 240, 430-434). The construct ALG242 was co-transformed with ALG 363 and transgenic plants were selected on medium supplemented with 10 nm of chlorsulfuron. A number of resistant plants were recovered, confirming introduction of mutation into the endogenous gene of *Arabidopsis* using our gene targeting system. PCR and sequencing analysis, have confirmed presence of mutation.

Similar data were observed in tobacco for uidA gene repair and ALS mutagenesis using the ALG460 construct (FIG. 7)

To assess efficiency of gene targeting in rice a set of constructs were prepared based on the viral origin of replication and replicase from maize streak virus (MSV) (FIG. 8). A premature stop codon in magnesium chelatase fragment of rice (Acc. No. EF065607) was introduced and cloned into vector with MSV origins of replication (ALG462). The replicase source was co-delivered using ALG463 vector. Mutation in the gene is affecting the colour of the leaf tissue from green to light green or white. Numerous sectors of light green or white colours were observed in targeted lines, confirming that the method is efficient in rice. Sequencing analysis has confirmed mutations in affected leaf sectors.

tnpA Domain tnpA domain of En/Spm transposable element (Acc. No. M25427) was amplified from maize cDNA library using the following primers:

```
                               SEQ ID NO. 1
AS900 gctcgagaacatgttcaggatggattcgtct SEQ ID NO. 2
AS101 cgcggatccgcgcatttgccctcctatcacac SEQ ID NO. 3
atgttcaggatggattcgtctggcaggagatccagatcacgaaggtcga ggggttccagtggtgctcctaacatgtttgagggcaccacaacaagcag aagcaggcaagagcagttgcttgcctcccttgagcagatgcggggtagc agcggaccctccaatacagaagggactacttcgcgtgccgctgatttgg tggcacctactatggcacctactgcggaggcagctgtggacgcggaggc agctgtggacgcggaggctgaggaagctgccgcagaactggacgatgga gaggagacttcgggagcagacgcttctacagaggaggctgccacacagg ctccgccacggcgtgccatcagatatcgtcggtccctcacattgaagcc ttctaaaccccttcgatcaacggagggttattgaaccgaaaggcaccagg gcgtggaaggaggtcagttgggacggaacagggcatcgcacaccaatcc tcacagagttggggatttgtttgcgattcgcctacccggcgatggtgac agagggcggtcaagagatagctgctcattactgggctcattgggatctc aagccgtacgggaacgacgggacacacacaagcaaagtgtgggatttgt tttggggccaatttcgcgtgtgcgaccccctataccttggatgattcata tgtgcgtgaggtattcaatggctcagcagatagagctgtaaagggaatg atgtataaagcacgattgagggccgtcacggtgtaccaaaagcgtcagg ggaactattgtgacgcgaatatggcaaaggaaattcacctgacggctca gcagtacaaagagagtgaggtggattggttgagccaccattcggatgct
```

-continued

```
tgggcgtggatgtgcgagtattgggcttctgaggagttcttggccatat ctaatagaaatcgtatgaatcggttgagcaagccaggggtccacttctt cggggcggatggacacgttggcaaggctgcacgtatggcggctcgaaat ggagtggagcctactttgcttcaagtcttcgtcgagggacacaagggtc ccgatccgaatcatccggaaatactgaatgacagtaatgcgacagagaa actggctcgctacattgacaacgtgagagaaaaaaatggtccagacacg gattggctcactggagagttcgatacggaggcggcttataaggctggtg gaggcgtaccacatgggaggttagcaattggtgacggtgttgtccccg tcggagttacactagacggtccaatttctcagctgggtcgaatcgaccc cgacgaccatctgcacgtgaaggagagctgcttgagaagatgactcaga tggaggagagtatggcgcaatataagcaacaagtgcagcaacagatgca acaaatgcaaaattggatgctacatcagatgtatggaggtgccggaact cagttcggcatgccgccttttcaacaacccctatcatcacacatccgg tgtctggacaatcatcggaccgctccactgcagcggcagatggatcaca gggttctgcaacttctgtccaagaccaattgatgccattgggtgtgatc ggcgggcaaatgcgcggatcc
``` recA Domain of recA Gene

SEQ ID NO. 4

```
ggtaacctgaagcagtccaacacgctgctgatcttcatcaaccagat ccgtatgaaaattggtgtgatgttcggtaacccggaaaccactaccg gtggtaacgcgctgaaattctacgcctctgttcgtctcgacatccgt cgttac
```

The recA domain (SEQ ID NO.4) of the recA gene was amplified from genomic DNA of JM101 (New England Biolabs) *E. coli* strain using the following primers:

```
AS380  cgggatccggtaacctgaagcagtccaaca   SEQ ID NO. 5

AS381  cggtctagatttaacgacggatgtcgagac   SEQ ID NO. 6
       ga
``` virD2-Nuclear Localisation Sequence (virD2NLS)

The nuclear localisation sequence of a virD2 gene was amplified from *Agrobacterium* strain GV3101 using the following primers:

```
AS380
                                        SEQ ID NO. 5
cgggatccggtaacctgaagcagtccaaca AS881
                                        SEQ ID NO. 7
ctctcgcgtttgcgttcactcggttctccatcatcatcttcacgcggac AS882
                                        SEQ ID NO. 8
cactagttcatctctcgcgtttg AS899
                                        SEQ ID NO. 9
ccatcatcatcttcacgcggacgcttgtaacgacggatgtcgagacga
```

Nuclear Localisation Sequence of virD2

SEQ ID NO. 10

```
aagcgtccgcgtgaagatgatgatggagaaccgagtgaacgcaaacg cgagagatga
``` tNpA-recA-virD2NLS Domain Fusion

The recA domain is underlined; nuclear localisation sequence from virD2 gene is in italic.

SEQ ID NO. 11

```
atgttcaggatggattcgtctggcaggagatccagatcacgaaggtcg aggggttccagtggtgctcctaacatgtttgagggcaccacaacaagc agaagcaggcaagagcagttgcttgcctcccttgagcagatgcgggt agcagcggaccctccaatacagaagggactacttcgcgtgccgctgat ttggtggcacctactatggcacctactgcggaggcagctgtggacgcg gaggcagctgtggacgcggaggctgaggaagctgccgcagaactggac gatggagaggagacttcgggagcagacgcttctacagaggaggctgcc acacaggctccgccacggcgtgccatcagatatcgtcggtccctcaca ttgaagccttctaaacccttcgatcaacggagggttattgaaccgaaa ggcaccagggcgtggaaggaggtcagttgggacggaacagggcatcgc acaccaatcctcacagagttggggatttgtttgcgattcgcctacccg gcgatggtgacagagggcggtcaagagatagctgctcattactgggct cattgggatctcaagccgtacgggaacgacgggacacacacaagcaaa gtgtgggatttgttttggggccaatttcgcgtgtgcgacccctatacc ttggatgattcatatgtgcgtgaggtattcaatggctcagcagataga gctgtaaagggaatgatgtataaagcacgattgagggccgtcacggtg taccaaaagcgtcaggggaactattgtgacgcgaatatggcaaaggaa attcacctgacggctcagcagtacaaagagagtgaggtggattggttg agccaccattcggatgcttgggcgtggatgtgcgagtattgggcttct gaggagttcttggccatatctaatagaaatcgtatgaatcggttgagc aagccaggggtccacttcttcggggcggatggacacgttggcaaggct gcacgtatggcggctcgaaatggagtggagcctactttgcttcaagtc ttcgtcgagggacacaagggtcccgatccgaatcatccggaaatactg aatgacagtaatgcgacagagaaactggctcgctacattgacaacgtg agagaaaaaaatggtccagacacggattggctcactggagagttcgat acggaggcggcttataaggctggtggaggcgtaccacatgggaggtta gcaattggtgacggtgttgtccccgtcggagttacactagacggtcc aatttctcagctgggtcgaatcgaccccgacgaccatctgcacgtgaa ggagagctgcttgagaagatgactcagatggaggagagtatggcgcaa tataagcaacaagtgcagcaacagatgcaacaaatgcaaaattggatg ctacatcagatgtatggaggtgccggaactcagttcggcatgccgcct tttcaacaaccccctatcatcacacatccggtgtctggacaatcatcg gaccgctccactgcagcggcagatggatcacagggttctgcaacttct
```

-continued
gtccaagaccaattgatgccattgggtgtgatcggcgggcaaatgcgc ggatccggtaacctgaagcagtccaacacgctgctgatcttcatcaac cagatccgtatgaaaattggtgtgatgttcggtaacccggaaaccact accggtggtaacgcgctgaaattctacgcctctgttcgtctcgacatc cgtcgttacaagcgtccgcgtgaagatgatgatggagaaccgagtgaa cgcaaacgcgagagatga Atabidopsis Ubiquitin 3 Promoter Promoter sequence for *Arabidopsis* ubiquitin 3 gene (At5g03250) was amplified from genomic DNA of *Arabidopsis* Col-0 strain using the following primers:

```
AS724
                                              SEQ ID NO. 12
cggtacctaccggatttggagccaagtc AS726
                                              SEQ ID NO. 13
gctcgagtgtttggtgacctgaaataaaacaatagaacaagt SEQ ID NO. 14
taccggatttggagccaagtctcataaacgccattgtggaagaaa
gtcttgagttggtggtaatgtaacagagtagtaagaacagagaag
agagagagtgtgagatacatgaattgtcgggcaacaaaaatcctg
aacatcttattttagcaaagagaaagagttccgagtctgtagcag
aagagtgaggagaaatttaagctcttggacttgtgaattgttccg
cctcttgaatacttcttcaatcctcatatattcttcttctatgtt
acctgaaaaccggcatttaatctcgcgggtttattccggttcaac
attttttttgttttgagttattatctgggcttaataacgcaggcc
tgaaataaattcaaggcccaactgttttttttttaagaagttgc
tgttaaaaaaaaaaagggaattaacaacaacaacaaaaaaga
taaagaaataataacaattactttaattgtagactaaaaaaaca
tagattttatcatgaaaaaagagaaaagaaataaaaacttggat
caaaaaaaaaacatacagatcttctaattattaacttttcttaaa
aattaggtcctttttcccaacaattaggtttagagtttggaatt
aaaccaaaaagattgttctaaaaaatactcaaatttggtagataa
gtttccttattttaattagtcaatggtagatacttttttttcttt
tctttattagagtagattagaatcttttatgccaagtattgataa
attaaatcaagaagataaactatcataatcaacatgaaattaaaa
gaaaaatctcatatatagtattagtattctctatatatattatga
ttgcttattcttaatgggttgggttaaccaagacatagtcttaat
ggaaagaatctttttttgaacttttccttattgattaaattcttc
tatagaaaagaaagaaattatttgaggaaaagtatatacaaaaag
aaaaatagaaaaatgtcagtgaagcagatgtaatggatgacctaa
tccaaccaccaccataggatgtttctacttgagtcggtctttttaa
aaacgcacggtggaaaatatgacacgtatcatatgattccttcct
ttagtttcgtgataataatcctcaactgatatcttccttttttg
ttttggctaaagatattttattctcattaatagaaaagacggttt
tgggcttttggtttgcgatataaagaagaccttcgtgtggaagat
aataattcatccttcgtctttttctgactcttcaatctctccca
aagcctaaagcgatctctgcaaatctctcgcgactctctctttca
aggtatattttctgattcttttttgtttttgattcgtatctgatct
ccaatttttgttatgtggattattgaatcttttgtaaaattgct
tttgacaatattgttcgtttcgtcaatccagcttctaaattttgt
cctgattactaagatatcgattcgtagtgtttacatctgtgtaat
ttcttgcttgattgtgaaattaggattttcaaggacgatctattc
aattttttgtgttttctttgttcgattctctctgttttaggttttct
tatgtttagatccgtttctctttggtgttgttttgatttctctta
cggcttttgatttggtatatgttcgctgattggtttctacttgtt
ctattgttttatttcaggtcaccaaaca
```

Ags Terminator

The agropine synthase polyA signal (ags terminator) was synthesized based on the gene bank sequence EU181145.

```
                                              SEQ ID NO. 15
Gaattaacagaggtggatggacagacccgttcttacaccggactgg gcgcgggataggatattcagattgggatgggattgagcttaaagcc ggcgctgagaccatgctcaaggtaggcaatgtcctcagcgtcgagc
```

-continued
```
ccggcatctatgtcgagggcattggtggagcgcgcttcggggatac cgtgcttgtaactgagaccggatatgaggccctcactccgcttgat cttggcaaagatatttgacgcatttattagtatgtgttaattttca tttgcagtgcagtattttctattcgatctttatgtaattcgttaca attaataaatattcaaatcagattattgactgtcatttgtatcaaa tcgtgtttaatggatattttattataatattgatgat
```

BCTVi Sequence

The beet curly top virus (BCTV, Acc. No. BCTCG028A) repA replicase gene and genes responsible for regulation of viral replication were amplified using the following set of primers:

```
                                              SEQ ID NO. 16
AS710   aagcttgggaagtatgaagacgtgaag SEQ ID NO. 17
AS711   tttttttcgggccatccggtttatgaaagttgtactaatatat SEQ ID NO. 18
AS712   accggatggcccgaaaaaaatg SEQ ID NO. 19
AS713   ggtaccttataattacatatacatgta
```

The stem loop in the promoter region of repA gene was partially deleted by overlapping primers AS711 and AS712 to prevent replication of this cassette in the plant cells.

Two introns from the *Arabidopsis* gene At2g29890 were inserted into the sequence to improve expression efficiency in plants and to prevent replication of the repair cassette in *Agrobacterium* cells (underlined). The following overlapping primers were used to introduce these introns into the BCTVi sequence:

```
AS795
                                              SEQ ID NO. 20
aggccaaacaaagatgaaaattacctggttggggataccaggtcgaat AS796
                                              SEQ ID NO. 21
attcgacctggtatccccaaccaggtaattttcatctttgtttggcct AS797
                                              SEQ ID NO. 22
atgtttggatggaaatgtgctgacctgcaatctcataagtacaatgga AS798
                                              SEQ ID NO. 23
tccattgtacttatgagattgcaggtcagcacatttccatccaaacat
``` for intron 1, and

```
AS799
                                              SEQ ID NO. 24
tcaagatgggaaaagatttcttaccttcaagaaacggggtccagtcaa AS800
                                              SEQ ID NO. 25
ttgactggaccccgtttcttgaaggtaagaaatcttttcccatcttga AS801
                                              SEQ ID NO. 26
tatctctagtctcttttcaagacctgcaatgttccacgcatattat
```

AS802

SEQ ID NO. 27
ataatatgcgtggaaacattgcaggtcttgaaaaagagactagagata for intron 2.

SEQ ID NO. 28
ttataattacatatacatgtaaaaataacgtatataaaacgacataa
ttcaaaacttgctgagcaagtttcctgtggggcacacttactttact
tttactaaagtaaagttactttaataaagttgtcccctctttttgac
cagtcaacaaatcttatctgaaaggaatcttcttcaggaagtttccc
gcaggaatcttcttcaggaagtttcccgctcaaaaacgtcacatcat
tcaacagtcccctccacgtgtcacgttttgattgggtgcccatttt
tttcgggccatccggtttatgaaagttgtactaatatatataatact
ccaatactccaatagatatgttaatatgctaagccacgtcatcggag
tacaatgcctcctactaaaagatttcgtattcaagcaaaaacatat
ttcttacatatcctcagtgttctctttcaaaagaagaagctcttgag
caaattcaaagaatacaactttcatctaataaaaaatatattaaaat
tgccagagagctacacgaagatgggcaacctcatctccacgtcctgc
ttcaactcgaaggaaaagttcagatcacaaatatcagattattcgac
ctggtatccccaaccaggtaattttcatctttgtttggccttccaag
tgcttttttttgctgtttacgggtggaacttcagtaaaaatgggatca
aaacatcatatggcataaataaattttaagaatggcgaactcggggt
taccgaatatggcttccttttttcagtgtttcttagtccattgtactt
atgagattgcaggtcagcacatttccatccaaacattcagagagcta
aatccagctccgacgtcaagtcctacgtcgacaaggacggagacaca
attgaatggggagaattccagatcgacggtagaagtgctagaggagg
tcaacagacagctaacgactcatatgccaaggcgttaaacgcaactt
ctcttgaccaagcacttcaaatattgaaggaagaacaaccaaaggat
tacttccttcaacatcacaatcttttgaacaatgctcaaaagatatt
tcagaggccacctgatccatggactccactatttcctctgtcctcat
tcacaaacgttcctgaggaaatgcaagaatgggctgatgcatatttc
ggggttgatgccgctgcgcggcctttaagatataatagtatcatagt
agagggtgattcaagaacagggaagactatgtgggctagatctttag
gggcccacaattacatcacagggcacttagattttagccctagaacg
tattatgatgaagtggaatacaacgtcattgatgacgtagatcccac
ttacttaaagatgaaacactggaaacaccttattggagcacaaaagg
agtggcagacaaacttaaagtatggaaaaccacgtgtcattaaaggt
ggtatccctgcattatattatgcaatccaggacctgagagctcata
ccaacaatttcttgaaaaaccagaaaatgaagcccttaagtcctgga
cattacataattcaaccttctgcaaactccaaggtccgctctttaat
aaccaagcagcagcatcctcgcaaggtgactctaccctgtaactgcc
acttcacaatacaccatgaatgtaatagaggattttcgcacaggga acctattactctccatcaggcaacaaattccgtcgaattcgagaatg
taccgaatccactgtatatgaaactcctatggttcgagagatacggg
ccaatctatcaactgaagatacaaatcagattcaactacaacctccg
gagagcgttgaatcttcacaagtgctggatagagctgacgataactg
gatcgaacaggatattgactggaccccgtttcttgaag<u>gtaagaaat</u>
<u>cttttcccatcttgaagtcacctcaaaccgaacgttaggaaattcca</u>
<u>aaatgttttgatagtagtctacttagtttcaagttttgggtttgtgt</u>
<u>atactttcactaataatatgcgtggaaacattgcaggtcttgaaaaa</u>
gagactagagatatacttggataatctaggtttaatttgtattaata
atgtaattagaggtttaaatcatgtcctgtatgaagaatttactttt
gtatcaagtgtaattcagaaccagagtgttgcaatgaacttgtacta
atttcattattaataataaatattattaataaaaatagcatctacaa
ttgccaaataatgtggcatacatattagtattatccgtattatcatt
aacaacaacatagagtaaagcattctccttcacgtcttcatacttcc
ca uidA Mutated Gene

A two base pair deletion (GT-deletion) was introduced into the uidA gene from *E. coli*, generating a frame shift in the uidA ORF. The position of deletion is between two nucleotides, and shown in capital letter and underlined.

SEQ ID NO. 29
atgttacgtcctgtagaaaccccaacccgtgaaatcaaaaaactcga
cggcctgtgggcattcagtctggatcgcgaaaactgtggaattgatc
agcgttggtgggaaagcgcgttacaagaaagccgggcaattgctgtg
ccaggcagttttaacgatcagttcgccgatgcagatattcgtaatta
tgcgggcaacgtctggtatcagcgcgaagtctttataccgaaaggtt
gggcaggccagcgtatcgtgctgcgtttcgatgcggtcactcattac
ggcaaagtgtgggtcaataatcaggaagtgatggagcatcagggcgg
ctatacgccatttgaagccgatgtcacgccgtatgttattgccggga
aaagTAcgtatcaccgtttgtgtgaacaacgaactgaactggcagac
tatcccgccgggaatggtgattaccgacgaaaacggcaagaaaaagc
agtcttacttccatgatttctttaactatgccggaatccatcgcagc
gtaatgctctacaccacgccgaacacctgggtggacgatatcaccgt
ggtgacgcatgtcgcgcaagactgtaaccacgcgtctgttgactggc
aaggtggtggccaatggtgatgtcagcgttgaactgcgtgatgcggat
caacaggtggttgcaactggacaaggcactagcgggactttgcaagt
ggtgaatccgcacctctggcaaccgggtgaaggttatctctatgaac
tgtgcgtcacagccaaaagccagacagagtgtgatatctacccgctt
cgcgtcggcatccggtcagtggcagtgaagggcgaacagttcctgat
taaccacaaaccgttctactttactggctttggtcgtcatgaagatg
cggacttacgtggcaaaggattcgataacgtgctgatggtgcacgac
cacgcattaatggactggattggggccaactcctaccgtacctcgca -continued

```
ttacccttacgctgaagagatgctcgactgggcagatgaacatggca tcgtggtgattgatgaaactgctgctgtcggctttaacctctcttta ggcattggtttcgaagcgggcaacaagccgaaagaactgtacagcga agaggcagtcaacgggaaactcagcaagcgcacttacaggcgatta aagagctgatagcgcgtgacaaaaaccacccaagcgtggtgatgtgg agtattgccaacgaaccggataccgtccgcaagtgcacgggaatat ttcgccactggcggaagcaacgcgtaaactcgacccgacgcgtccga tcacctgcgtcaatgtaatgttctgcgacgctcacaccgataccatc agcgatctctttgatgtgctgtgcctgaaccgttattacggatggta tgtccaaagcggcgatttggaaacggcagagaaggtactggaaaaag aacttctggcctggcaggagaaactgcatcagccgattatcatcacc gaatacggcgtggatacgttagccgggctgcactcaatgtacaccga catgtggagtgaagagtatcagtgtgcatggctggatatgtatcacc gcgtctttgatcgcgtcagcgccgtcgtcggtgaacaggtatggaat ttcgccgattttgcgacctcgcaaggcatattgcgcgttggcggtaa caagaaagggatcttcactcgcgaccgcaaaccgaagtcggcggctt ttctgctgcaaaaacgctggactggcatgaacttcggtgaaaaaccg cagcagggaggcaaacaatga
```

CMV 35S Promoter

The mutated uidA gene was placed under control of the cauliflower mosaic virus (CMV) 35S promoter, which was synthesised base on the sequence available from gene databank (Acc.No. AF502128).

```
                                       SEQ ID NO. 30
caatcccacaaaaatctgagcttaacagcacagttgctcctctcaga gcagaatcgggtattcaacaccctcatatcaactactacgttgtgta taacggtccacatgccggtatatacgatgactggggttgtacaaagg cggcaacaaacggcgttcccggagttgcacacaagaaatttgccact attacagaggcaagagcagcagctgacgcgtacacaacaagtcagca aacagacaggttgaacttcatcccaaaggagaagctcaactcaagc ccaagagctttgctaaggccctaacaagcccaccaaagcaaaaagcc cactggctcacgctaggaaccaaaaggcccagcagtgatccagcccc aaaagagatctcctttgccccggagattacaatggacgatttcctct atctttacgatctaggaaggaagttcgaaggtgaagtagacgacact atgttcaccactgataatgagaaggttagcctcttcaatttcagaaa gaatgctgacccacagatggttagagaggcctacgcagcaggtctca tcaagacgatctacccgagtaacaatctccaggagatcaaataccct cccaagaaggttaaagatgcagtcaaaagattcaggactaattgcat caagaacacagagaaagacatatttctcaagatcagaagtactattc cagtatggacgattcaaggcttgcttcataaaccaaggcaagtaata gagattggagtctctaaaaaggtagttcctactgaatctaaggccat
```

```
gcatggagtctaagattcaaatcgaggatctaacagaactcgccgtg aagactggcgaacagttcatacagagtcttttacgactcaatgacaa gaagaaaatcttcgtcaacatggtggagcacgacactctggtctact ccaaaaatgtcaaagatacagtctcagaagaccaaagggctattgag acttttcaacaaaggataatttcgggaaacctcctcggattccattg cccagctatctgtcacttcatcgaaaggacagtagaaaaggaaggtg gctcctacaaatgccatcattgcgataaaggaaaggctatcattcaa gatctctctgccgacagtggtcccaaagatggaccccacccacgag gagcatcgtggaaaaagaagacgttccaaccacgtcttcaaagcaag tggattgatgtgacatctccactgacgtaagggatgacgcacaatcc cactatccttcgcaagacccttcctctatataaggaagttcatttca tttggagaggacacg
```

Nos Terminator

The nos teminator fragment was synthesised based on GenBank sequence accession EU048864.

```
                                       SEQ ID NO. 31
gtcaagcagatcgttcaaacatttggcaataaagtttcttaagatt gaatcctgttgccggtcttgcgatgattatcatataatttctgttg aattacgtgaagcatgtaataattaacatgtaatgcatgacgttat ttatgagatgggttttatgattagagtcccgcaattatacattta atacgcgatagaaaacaaaatatagcgcgcaaactaggataaatta tcgcgcgcggtgtcatctatgttactagatcgac
```

BCTV Viral Origin of Replication (VOR)

Viral origin of replication was amplified from viral DNA (Acc.No. BCTCG028A) with the following primers:

| AS252 | tgtactccgatgacgtggctt | SEQ ID NO. 32 |
|---|---|---|
| AS253 | ttcaggaagtttcccgctca | SEQ ID NO. 33 |

```
                                       SEQ ID NO. 34
tgtactccgatgacgtggcttagcatattaacatatctattggagt
attggagtattatatatattagtacaactttcataagggccatccg
ttataatattaccggatggcccgaaaaaaatgggcacccaatcaaa
acgtgacacgtggaaggggactgttgaatgatgtgacgttttgag
cgggaacttcctgaa
```

Sub Terminal Region 1 of Maize En/Spm Transposable Element (STR1)

The sequence for STR1 was amplified from maize genomic DNA using the following primers:

| AS150 | | SEQ ID NO. 35 |
|---|---|---|
| aggagtgtcagttaattaaaga | | |
| AS151 | | SEQ ID NO. 36 |
| gtcgactgtatactggacg | | |

```
                                       SEQ ID NO. 37
Gagtgtcagttaattaaagagtgtcggggccgacactcttaatcgaagt aaaagtgtgggttttgctgcaccgacactcttaatttaagagtgtcggg gtcccgatgaaaccgacgcttttaatttaagagtgtgggttttttccaca
```

-continued ccgacactcttatgaatgttaccctaaattccccaatcctattctacag ccgtcgtgcttcttctctcctttctccctgcccgccgtccagtataca

Sub Terminal Region 2 of Maize En/Spm Transposable Element (STR2)

The sequence for STR2 was amplified from maize genomic DNA using the following primers:

AS152　　　　　　　　　　　　　　　　SEQ ID NO. 38
agtgtcggccaaaacccac

AS153　　　　　　　　　　　　　　　　SEQ ID NO. 39
cacactcttatatgcgccag

SEQ ID NO. 40
ccactcttatatgcgcccaggtagcttactgatgtgcgcgcagtaagag tgacggccacggtactggccgacacttttaacataagagtgtcggttgc ttgttgaaccgacacttttaacataagagcgtcggtccccacacttcta tacgaataagagcgtccattttagagtgacggctaagagtgtcggtcaa ccgacactcttatacttagagtgtcggcttatttcagtaagagtgtggg gttttggccgacact uidA Repair Donor Sequence (uidA-R)

The donor sequence for uidA gene repair was amplified from *E. coli* genomic DNA strain DH10B using the following primers:

AS866　　　　　　　　　　　　　　　　SEQ ID NO. 41
ctgcgtttcgatgcggtcac

AS867　　　　　　　　　　　　　　　　SEQ ID NO. 42
accaatgcctaaagagaggtt

SEQ ID NO. 43
Ctgcgtttcgatgcggtcactcattacggcaaagtgtgggtcaataatc aggaagtgatggagcatcagggcggctatacgccatttgaagccgatgt cacgccgtatgttattgccgggaaaagtgtacgtatcaccgtttgtgtg aacaacgaactgaactggcagactatcccgccgggaatggtgattaccg acgaaaacggcaagaaaaagcagtcttacttccatgatttctttaacta tgccggaatccatcgcagcgtaatgctctacaccacgccgaacacctgg gtggacgatatcaccgtggtgacgcatgtcgcgcaagactgtaaccacg cgtctgttgactggcaggtggtggccaatggtgatgtcagcgttgaact gcgtgatgcggatcaacaggtggttgcaactggacaaggcactagcggg actttgcaagtggtgaatccgcacctctggcaaccgggtgaaggttatc tctatgaactgtgcgtcacagccaaaagccagacagagtgtgatatcta cccgcttcgcgtcggcatccggtcagtggcagtgaagggcgaacagttc ctgattaaccacaaaccgttctactttactggctttggtcgtcatgaag atgcggacttgcgtggcaaaggattcgataacgtgctgatggtgcacga ccacgcattaatggactggattggggccaactcctaccgtacctcgcat tacccttacgctgaagagatgctcgactgggcagatgaacatggcatcg tggtgattgatgaaactgctgctgtcggctttaacctctcttaggcat tggt

ALS Mutagenesis Sequence of *Arabidopsis* (ALS-M)

A mutated donor (C to T mutation is in capital and underlined) for targeting of *Arabidopsis* endogenous acetolactate synthase (ALS) gene was prepared using the following set of primers:

AS803　　　　　　　　　　　　　　　　SEQ ID NO. 44
gcggctgcagggcggcggcaacaacaacaacaa

AS804　　　　　　　　　　　　　　　　SEQ ID NO. 45
atctgtaccaatcatacgacgagagacttgtcctgtgattgctacaag AS805　　　　　　　　　　　　　　　　SEQ ID NO. 46
cttgtagcaatcacaggacaagtctctcgtcgtatgattggtacagat AS806　　　　　　　　　　　　　　　　SEQ ID NO. 47
accatctagaccaatctcagccgagtcaatatca SEQ ID NO. 48
gcggcggcaacaacaacaacaacaacatcttcttcgatctccttctcca ccaaaccatctccttcctcctccaaatcaccattaccaatctccagatt ctccctcccattctccctaaacccaacaaatcatcctcctcctcccgc cgccgcggtatcaaatccagctctccctcctccatctccgcgtgctca acacaaccaccaatgtcacaaccactccctctccaaccaaacctaccaa acccgaaacattcatctcccgattcgctccagatcaaccccgcaaaggc gctgatatcctcgtcgaagctttagaacgtcaaggcgtagaaaccgtat tcgcttaccctggaggtgcatcaatggagattcaccaagccttaacccg ctcttcctcaatccgtaacgtccttcctcgtcacgaacaaggaggtgta ttcgcagcagaaggatacgctcgatcctcaggtaaaccaggtatctgta tagccacttcaggtcccggagctacaaatctcgttagcggattagccga tgcgttgttagatagtgttcctcttgtagcaatcacaggacaagtcTct cgtcgtatgattggtacagatgcgtttcaagagactccgattgttgagg taacgcgttcgattacgaagcataactatcttgtgatggatgttgaaga tatccctaggattattgaggaagctttcttttttagctacttctggtaga cctggacctgttttggttgatgttcctaaagatattcaacaacagcttg cgattcctaattgggaacaggctatgagattacctggttatatgtctag gatgcctaaacctccggaagattctcatttggagcagattgttaggttg atttctgagtctaagaagcctgtgttgtatgttggtggtggttgtttga attctagcgatgaattgggtaggtttgttgagcttacggggatccctgt tgcgagtacgttgatgggctgggatcttatccttgtgatgatgagttg tcgttacatatgcttggaatgcatgggactgtgtatgcaaattacgctg tggagcatagtgatttgttgttggcgtttggggtaaggtttgatgatcg tgtcacgggtaagcttgaggcttttgctagtagggctaagattgttcat attgatattgactcggctgagattgg

APETALA 3 DNA Domain (AP3)

AP3 domain was amplified using the following primers:

AS690　　　　　　　　　　　　　　　　SEQ ID NO. 49
ctcgagactttccattttagtaactaccaccatgttacgtcctgtaga aacccca

```
AS300                           SEQ ID NO. 50
aattgtttgcctccctgctggcctt

SEQ ID NO. 51
agttactaaaaatggaaagt
```

APETALA1 DNA Binding Domain (AP1)

Ap1 domain was amplified from genomic DNA of *Arabidopsis* using the following primers:

```
AS429                           SEQ ID NO. 52
ggctcgagatgggaaggggtagggt

AS430                           SEQ ID NO. 53
catcgatttcggcgtaagagtacct

SEQ ID NO. 54
atgggaaggggtagggttcaattgaagaggatagagaacaagatcaata
gacaagtgacattctcgaaaagaagagctggtcttttgaagaaagctca
tgagatctctgttctctgtgatgctgaagttgctcttgttgtcttctcc
cataagggaaaactcttcgaatactccactgattcttgtatggagaaga
tacttgaacgctatgagaggtactcttacgccgaa
```

Primer Binding Sequence

Primer binding sequence from the tobacco tnt1 retrotransposon was amplified with the following primers:

```
AS912                           SEQ ID NO. 55
gccgcggctttattaccgtgaatatta

AS913                           SEQ ID NO. 56
cgcggccgctctgataagtgcaacctgatt

SEQ ID NO. 57
Gccgcggctttattaccgtgaatattattttggtaagggtttattccc
aacaactggtatcagagcacaggttctgctcgttcactgaaatactatt
cactgtcggtagtactatacttggtgaaaaataaaaatgtctggagtaa
agtacgaggtagcaaaattcaatggagataacggtttctcaacatggca
aagaaggatgagagatctgctcatccaacaaggattacacaaggttcta
gatgttgattccaaaaagcctgataccatgaaagctgaggattgggctg
acttggatgaaagagctgctagtgcaatcaggttgcacttatcagagcg
gccgcg
```

Reverse Transcriptase—RNaseH(RT-RH)

RT-RH was amplified from tobacco tnt1 retrotransposon using the following primers:

```
AS885                           SEQ ID NO. 58
tctcgagaacatgcagcatagagtctcatttc Tnt-RT-R                        SEQ ID NO. 59
ctagtttgaatgcattccgacaa SEQ ID NO. 60
atgtcagaaaaggtgaagaatggtataattcctaactttgttactattc
cttctacttctaacaatccacaagtgcagaaagtacgaccgacgaggt
ttccgagcaggggagcaacctggtgaggttattgagcaggggagcaa
cttgatgaaggtgtcgaggaagtggagcaccccactcagggagaagaac
aacatcaacctctgaggagatcagagaggccaagggtagagtcacgcag
gtacccttccacagagtatgtcctcatcagtgatgaggggagccagaa
agtcttaaggaggtgttgtcccatccagaaaagaaccagtggatgaaag
ctatgcaagaagagatggaatctctccagaaaaatggcacatacaagct
ggttgaacttccaaagggtaaaagaccactcaaatgcaaatgggtcttt
aaactcaagaaagatggagatggcaagctggtcagatacaaagctcgat
tggtggttaaaggcttcgaacagaagaaaggtattgattttgacgaaat
tttctccccgttgttaaaatgacttctattcgaacaattttgagctta
gcagctagcctagatcttgaagtggagcagttggatgtgaaaactgcat
ttcttcatggagatttggaagaggagatttatatggagcaaccagaagg
atttgaagtagctggaaagaaacacatggtgtgcaaattgaataagagt
ctttatggattgaagcaggcaccaaggcagtggtacatgaagtttgatt
cattcatgaaaagtcaaacatacctaaagacctattctgatccatgtgt
atacttcaaaagattttctgagaataactttattatattgttgttgtat
gtggatgacatgctaattgtaggaaaagacaaggggttgatagcaaagt
tgaaaggagatctgtccaagtcatttgatatgaaggacttgggcccagc
acaacaaattctagggatgaagatagttcgagagagaacaagtagaaag
ttgtggctatctcaggagaagtacattgaacgtgtactagaacgcttca
acatgaagaatgctaagccagtcagcacacctcttgctggtcatctaaa
gttgagtaaaaagatgtgtcctacaacagtggaagagaaagggaacatg
gctaaagttccttattcttcagcagtcggaagcttgatgtatgcaatgg
tatgtactagacctgatattgctcacgcagttggtgttgtcagcaggtt
tcttgaaaatcctggaaaggaacattgggaagcagtcaagtggatactc
aggtacctgagaggtaccacgggagattgtttgtgctttggaggatctg
atccaatcttgaagggctatacagatgctgatatggcaggtgacattga
caacagaaaatccagtactggatatttgtttacattttcaggggagct
atatcatggcagtctaagttgcaaaagtgcgttgcactttcaacaactg
aagcagagtacattgctgctacagaaactggcaaggagatgatatggct
caagcgattccttcaagagcttggattgcatcagaaggagtatgtcgtc
tattgtgacagtcaaagtgcaatagaccttagcaagaactctatgtacc
atgcaaggaccaaacacattgatgtgagatatcattggattcgagaaat
ggtagatgatgaatctctaaaagtcttgaagatttctacaaatgagaat
cccgcagatatgctgaccaaggtggtaccaaggaacaagttcgagctat
gcaaagaacttgtcggaatgcattcaaactag
```

ALS Mutagenesis Sequence of Tobacco

A mutated donor for targeting of tobacco endogenous acetolactate synthase (ALS) gene was prepared using the following set of primers:

```
                                SEQ ID NO. 61
AS1031  gcccgggtcctccaccctcctccctagat SEQ ID NO. 62
AS1034  atcctacgtgccacttgaccggttatagcaa
```

-continued

AS1035 cggtcaagtggcacgtaggatgatcggtact        SEQ ID NO. 63

AS1036 atctagaacctggatagcatat        SEQ ID NO. 64

The mutation inducing chlorsulfuron resistance is capitalised (see below) and underlined.

SEQ ID NO. 65
gcccgggtcctccaccctcctccctagatccaccttcccttcccccac
cacccccacaaaaccaccccaccacccctccacctcaccccacccaca
ttcacagccaacgccgtcgtttcaccatctccaatgtcatttccactac
ccaaaaagtttccgagacccaaaaagccgaaactttcgtttcccgtttt
gcccctgacgaacccagaaagggttccgacgttctcgtggaggccctcg
aaagagaagggttacggacgttttttgcgtacccaggcggcgcttccct
cgagattcaccaagctttgacgcgctcaagcatcatccgcaacgtgcta
ccacgtcacgagcagggtggtgtcttcgccgctgagggttacgcacgcg
ccaccggcttccccggcgtttgcattgccacctccggccctggcgccac
caatctcgtcagtggcctcgcggacgccctactggatagcgtccccatt
gttgctataaccggtcaagtgGcacgtaggatgatcggtactgatgctt
ttcaggaaactccgattgttgaggtaactagatcgattaccaagcataa
ttatctcgttatggacgtagaggatattcctagggttgtacgtgaggct
tttttccttgcgagatcgggccggcctggccctgttttgattgatgtac
ctaaggatattcagcaacaattggtgatacctgactgggatcagccaat
gaggttgcctggttacatgtctaggttacctaaattgcccaatgagatg
tctttagaacaaatgttaggcttattctgagtcaaagaagcctgttt
tgtatgtggggggtgggtgttcgcaatcgagtgaggagttgagacgatt
cgtggagctcaccggtatcccgtggcaagtactttgatgggtcttgga
gcttttccaactggggatgagctttcccttcaatgtgggtatgcatg
gtactgtttatgctaattatgctgtggacagtagtgatttattgctcgc
atttggggtgaggtttgatgatagagttactggaaagttagaagctttt
gctagccgagcgaaaattgttcacattgatattgattcagctgagattg
gaaagaacaagcagcctcatgtttccatttgtgcggatatcaagttggc
gttacagggtttgaattcgatattggagagtaaggaaggtaaactgaag
gttggattttctgcttggaggcaggagttacggtgcagaaagtgaagt
acccgttgaattttaaaacttttggtgatgctattcctccgcaatatgc
tatccaggttctagat Maize streak virus (MSV) origin of replication for gene targeting in monocots was amplified with the following primers:

AS1020        SEQ ID NO. 66
gggtaccccgacgacggaggttgaggct

AS1021        SEQ ID NO. 67
cgaattcatgggctgctttagataaatc
and

AS1022        SEQ ID NO. 68
ttctagaccgacgacggaggttgaggct

AS1023        SEQ ID NO. 69
cccgcggatgggctgctttagataaatc

SEQ ID NO. 70
Ccgacgacggaggttgaggctgagggatggcagactgggagctccaaac
tctatagtatacccgtgcgccttcgaaatccgccgctcccttgtcttat
agtggttgcaaatgggccggaccgggccggcccagcaggaaaagaaggc
gcgcactaatattaccgcgccttcttttcctgcgagggcccggtagggc
ccgagcgatttgatgtaaagtttggtcctgctttgtatgatttatctaa
agcagcccat The MSV replicase was amplified using the following primers:

AS965 ggaattcatgaatgaatcgcacttgttag        SEQ ID NO. 71

AS966 actaatattacgagggcccggtagggcccgag        SEQ ID NO. 72

AS967 accgggccctcgtaatattagtgcgcgccttc        SEQ ID NO. 73

AS968 cggtaccgagtgttggcaaccagtaatga        SEQ ID NO. 74

AS1039 gtgtttgagagaggtatgtaaatatgaactgtat        SEQ ID NO. 75

AS1040 catatttacatacctctctcaaacacagccagag        SEQ ID NO. 76

AS1041 gtataacttgcaggtactttcattcctaggaagt        SEQ ID NO. 77

AS1042 ggaatgaaagtacctgcaagttatacgatcagga        SEQ ID NO. 78

The right side of stem loop in promoter region was eliminated to prevent recombination with origin of replication and a rice intron from alpha tubulin was inserted into the RepA gene. The intron sequence is in italics and underlined.

SEQ ID NO.79
ggaattcatgaatgaatcgcacttgttaggcaatttatagtgaccggga
ccggattctttagaatgggctgctttagataaatcatacaaagcaggac
caaactttacatcaaatcgctcgggccctaccgggccctcgtaatatta
gtgcgcgccttcttttcctgctgggccggcccggtccggcccatttgca
accactataagacaagggagcggcggatttcgaaggcgcacgggtatac
tatagagtttggagctcccagtctgccatccctcagcctcaacctccgt
cgtcggcaatggcctcctcctcatccaaccgtcagttctcacaccggaa
cgctaacacgttcctaaccctatccaaagtgtccagaaaatcctgaaatc
gcctgtcagatgatctgggagctcgttgttcgttggattcccaaataca
ttctatgtgcccgagaggcacataaagatggaagtttgcatttacatgc
attgcttcagacagagaagccggtaaggatatctgactcaaggttcttt
gatataaatgggtttcacccaaatattcagagtgccaagtcagtaaaca
gggtgagggattacattctcaaggaacctctggctgtgtttgagagag -continued <u>tatgtaaatatgaactgtatatgacaagtctcactgccatgggttacgt</u>

<u>ttcaatcaagtccacaagtgataaatattgtcctgatcgtataacttgc</u> ag gtactttcattcctaggaagtcccccttcctaggaaaatctgattca gaggtaaaggaaaaaaagccttctaaagatgaaataatgcgagacatta tttcacacgctacttccaaagaagagtacctctccatgatccagaaaga gcttcccctttgattggtccacaaaattgcagtattttgaatactctgca aataagcttttcctgagattcaggaagagttcaccaatcctcatccac cctcatcacctgatttactttgtaatgagtcaatcaatgattggctcca gcctaacatcttccaggttagtcccgaagcttacatgctccttcaacct tacctgttataccctcgaggatgcaatttctgacctccaatggatggat tctgtatccagtcacagatgaaagatcaagaaagcagagcctctacatc gtcggcccaacaagaaccggaaaatctacttgggccagaagcctagggg ttcataattactggcaaaataatgttgattggtcttcatacaacgaaga cgcaatctataacatcgtagatgatattccgtttaaattctgtccttgt tggaaacagttagttggctgtcagagggatttcattgtaaaccccaagt atggtaaaagaaaaaggtgcagaagaagtctaagcctacaataatcct cgccaactcggatgaagattggatgaaggaaatgactccagggcagctg gagtatttcgaggcaaactgcatcatttacattatgtcgccgggggaga aatggtattctcccctgagctgcctcctacggaggcagtacattcaga tagatcttgattttcgatgttctgcccgccgagcaccacccttagccg cccgccgactacccccctgtattgattgtgtgtttttcgtgccatcg cacgacatattaatgtaagctttcagcattcatcagatataataaaaac ggcgttttattcattactggttgccaacactcggtaccg A fragment of magnesium chelatase gene (MgChe) from rice was used for gene targeting in rice. It was amplified from japonica rice (Nipponbare) using the following primers:

SEQ ID NO. 80
AS1011 gctgcag atcgtggggcaggacgagatga

SEQ ID NO. 81
AS1012 ggcgcgccgtgggagatggagataccctc

SEQ ID NO. 82
AS1013 ggcgcgcccctgctcggttcatcctcat

SEQ ID NO. 83
AS1014 gactagt aagacttcataaaacttctcaa

A premature stop codon was introduced into the frame to generate a mutated phenotype.

SEQ ID NO. 84
Gctgcagatcgtggggcaggacgagatgaagctgtgcctgctgctcaac gtcatcgaccctaagatcggcggtgtcatgatcatgggagaccgtggca ccggcaaatccaccaccgtccgctcgctcgtcgacctgctcccggatat ccgcgtcgttgttggcgaccctttcaattccgaccctgacgatcccgag gtcatgggccctgaggtccgggaacgcgtgctggagggtgagaagcttc ctgttgtcacggccaagatcaccatggtagatcttcccttggtgccac tgaggatagagtctgtggcaccattgatattgagaaggcgctcaccgat ggtgtcaaggcgttcgagcctggtttgcttgccaaggccaacaggggga ttctttatgtggatgaggtcaatttgttggatgaccatctagtagatgt gcttctggattctgctgcgtcaggatggaacaccgtggagagagagggt atctccatctcccacggcgcgcccctgctcggttcatcctcattgggt ctggtaaccccgaggaaggggagctccggccacagctgcttgaccggtt tggcatgcacgcgcaggttggtactgtcagggatgctgaactcagggtg aaaattgttgaagagagagctcggttcgacagggatccaaaggcgttcc gtgagtcctacttggaggaacaagacaagctccagcagcagatttcatc tgctcggagtaaccttggtgctgtgcagattgaccatgatcttcgtgtt aagatttctaaagtgtgtgcagagttgaatgttgatggattaagagggg acattgtgactaacagggctgccaaggcgttggcagcactcaaaggcag ggacactgtcactgtagaggacattgccactgttatccccaactgcttg aggcatcggcttcggaaggacccacttgaatcaattgactcaggattgc tcgtggttgagaagttttatgaagtcttactagtg

The invention claimed is:

1. An isolated nucleic acid molecule that encodes for a chimeric multi domain recombination protein that is able to initiate strand invasion and annealing between single stranded DNA and target DNA in a plant cell and has the functions of:
   i) donor DNA-Binding;
   ii) chromosomal binding;
   iii) chromosomal target binding; and
   iv) recombination induction,
   wherein the multi domain recombination protein comprises a recombination induction domain selected from:
   (a) RecA, Rad51 or Rad52; or
   (b) a peptide domain of 15 to 50 amino acids from RecA, Rad51 or Rad52, which has recombination inducing activity.

2. A method of transforming a plant cell that comprises:
   1) introducing into the said plant cell a nucleic acid molecule that comprises a plant nuclear promoter operably linked to a first nucleic acid sequence that comprises the nucleic acid molecule according to claims 1; and
   2) introducing into the said plant cell a second nucleic acid molecule that comprises
      i) a donor nucleic acid sequence that is single stranded;
      ii) at least two flanking nucleic acid sequences that are capable of binding to a donor binding domain of the said multi domain recombination protein that are located adjacent to each end of the donor polynucleotide sequence forming left and right borders thereto.

3. The method according to claim 2, wherein the second nucleic acid molecule further comprises two viral origins of replication located 5' and 3' of the said left and right borders, respectively.

4. The method according to claim 3, further comprising introducing a nucleic acid molecule that comprises one of a plant nuclear promoter and a viral native promoter operably linked to a third nucleic acid sequence that encodes for a viral replicase protein.

5. The method according to claim 3, wherein said second nucleic acid molecule is operably linked to a plant nuclear promoter and further comprises a primer binding site that is fused to the 3' end of a right flanking border nucleic acid molecule.

6. The method according to claim 5, further comprising introducing a nucleic acid sequence that comprises a plant nuclear promoter operably linked to a third nucleic acid sequence that encodes for a reverse transcriptase protein.

7. The method according to claim 5, wherein the primer binding site is selected from a retrotransposon specific primer binding site, and a primer binding site of a retrovirus.

8. The method according to claim 6, wherein said third nucleic acid sequence is selected from the group of DNA encoding retrotransposon RNA, DNA encoding retroviral RNA and reverse transcriptase-RNase H.

9. A plant cell comprising a chimeric multi domain recombination protein that is able to initiate strand invasion and annealing between single stranded DNA and target DNA in a plant cell and has the functions of:
   i) donor DNA-Binding;
   ii) chromosomal binding,
   iii) chromosomal target binding; and
   iv) recombination induction,
   wherein the multi domain recombination protein comprises a recombination induction domain selected from:
   (a) RecA, Rad51 or Rad52; or
   (b) a peptide domain of 15 to 50 amino acids from RecA, Rad51 or Rad52, which has recombination inducing activity.

10. The plant cell according to claim 9, wherein the plant cell is selected from tobacco (*Nicotiana tabacum*) and other *Nicotiana* species, *arabidopsis*, potato, corn(maize), canola (rape), rice, wheat, barley, *brassica* sp. selected from the group of cauliflower, broccoli (e.g. green and purple sprouting), cabbage (e.g. red, green and white cabbages), curly kale, Brussels sprouts, cotton, algae (e.g. blue green species), lemnaspora, or moss (e.g. *physcomitrella patens*), tomato, capsicum, squashes, sunflower, soyabean, carrot, melons, grape vines, lettuce, strawberry, sugar beet, peas, and sorghum.

11. A method of producing at least a heterologous or exogenous RNA species in a plant that comprises:
   1) introducing into a regenerable plant cell a nucleic acid molecule that comprises a plant nuclear promoter operably linked to a first nucleic acid sequence that comprises the nucleic acid molecule according to claim 1;
   2) introducing into the said regenerable plant cell a second nucleic acid molecule that comprises
      i) a donor nucleic acid sequence; and
      ii) at least two flanking nucleic acid sequences that are located adjacent to each end of the donor nucleic acid sequence forming left and right borders thereto; and
      iii) two viral origins of replication located 5' and 3' to each of the said left and right borders, respectively, wherein said second nucleic acid molecule is operably linked to a plant nuclear promoter; and
   3) introducing into the said regenerable plant cell a third nucleic acid molecule that encodes for a viral replicase protein, wherein the third nucleic acid molecule is operably linked to a plant nuclear or native viral promoter;
   4) growing said regenerable plant cell of steps 1) to 3);
   5) selecting a plant cell of 4);
   6) regenerating a plant from the plant cell of 5); and
   7) growing the plant of 6).

12. A method of producing at least a heterologous or exogenous RNA species in a plant that comprises:
   1) introducing into a regenerable plant cell a nucleic acid sequence that comprises a plant nuclear promoter operably linked to a first nucleic acid sequence that comprises the polynucleotide sequence according to claim 1;
   2) introducing into the said regenerable plant cell a second nucleic acid sequence that comprises
      i) a donor nucleic acid sequence;
      ii) at least two flanking sequences that are located adjacent to each end of the donor polynucleotide sequence forming left and right borders thereto, wherein said second nucleic acid sequence is operably linked to a plant nuclear promoter; and
      iii) a primer binding site that is fused to the 3' end of the said right flanking border sequence;
   3) introducing into the said regenerable plant cell a third nucleic acid sequence that encodes for a reverse transcriptase protein, wherein the third nucleic acid sequence is operably linked to a plant nuclear promoter;
   4) growing said regenerable plant cell of steps 1) to 3);
   5) selecting a plant cell of 4);
   6) regenerating a plant from the plant cell of 5); and
   7) growing the plant of 6).

13. An isolated nucleic acid molecule that comprises a donor nucleic acid sequence that is single stranded, at least two flanking nucleic acid sequences located adjacent to each end of the said donor nucleic acid sequence forming left and right borders thereto, and two viral origins of replication located 5' and 3' to each of the said left and right borders, respectively, wherein the viral origins of replication are arranged as direct repeats, for use in a method according to claim 2.

14. The isolated nucleic acid molecule according to claim 13, further comprising a third nucleic acid sequence that comprises one of a plant nuclear and viral native promoter operably linked to a first nucleic acid sequence that encodes for a viral replicase protein.

15. A nucleic acid vector suitable for transformation of a plant or bacterial cell, comprising the nucleic acid molecule according to claim 1.

16. A plant cell containing the nucleic acid molecule according to claim 1.

17. A host cell containing a nucleic acid vector according to claim 15.

18. The method of producing a plant cell according to claim 16, the method including incorporating said nucleic acid molecule into the cell by means of transformation.

19. A method of producing a host cell according to claim 17, the method including incorporating said nucleic acid vector into the cell by means of transformation.

20. A plant comprising a plant cell according to claim 16 that is selected from the group consisting of tobacco (*Nicotiana tabacum*), *Nicotiana benthamiana*, carrot, vegetable and oilseed *Brassica's*, melons, Capsicums, grape vines, lettuce, strawberry, sugar beet, wheat, barley, (corn)maize, rice, soybean, peas, sorghum, sunflower, tomato, cotton, and potato.

* * * * *